(12) United States Patent  (10) Patent No.: US 8,183,277 B2
Simmen et al.  (45) Date of Patent: May 22, 2012

(54) MACROCYLIC INHIBITORS OF HEPATITIS C VIRUS

(75) Inventors: Kenneth Alan Simmen, Tervuren (BE); Herman Augustinus De Kock, Arendonk (BE); Pierre Jean-Marie Bernard Raboisson, Sterrebeek (BE); Dominique Louis Nestor Ghislain Surleraux, Braine-le-château (BE); Wim Van De Vreken, Beveren (BE)

(73) Assignee: Tibotec Pharmaceuticals Ltd., Co Cork (IE)

( * ) Notice: Subject to any disclaimer, the term of this patent is extended or adjusted under 35 U.S.C. 154(b) by 586 days.

(21) Appl. No.: 11/995,560

(22) PCT Filed: Jul. 28, 2006

(86) PCT No.: PCT/EP2006/064818
§ 371 (c)(1),
(2), (4) Date: Jan. 14, 2008

(87) PCT Pub. No.: WO2007/014924
PCT Pub. Date: Feb. 8, 2007

(65) Prior Publication Data
US 2008/0262058 A1 Oct. 23, 2008

(30) Foreign Application Priority Data
Jul. 29, 2005 (EP) .................................. 05107072

(51) Int. Cl.
*A61K 31/407* (2006.01)
*C07D 487/04* (2006.01)
(52) U.S. Cl. ........................ 514/413; 540/461
(58) Field of Classification Search .................. 540/461
See application file for complete search history.

(56) References Cited

U.S. PATENT DOCUMENTS

| | | | |
|---|---|---|---|
| 5,484,801 A | 1/1996 | Al-Razzak | |
| 5,807,876 A | 9/1998 | Armistead et al. | |
| 5,948,436 A | 9/1999 | Al-Razzak | |
| 6,037,157 A | 3/2000 | Norbeck et al. | |
| 6,054,472 A | 4/2000 | Armistead et al. | |
| 6,344,465 B1 | 2/2002 | Armistead et al. | |
| 6,498,178 B2 | 12/2002 | Stamos et al. | |
| 7,666,834 B2 | 2/2010 | Simmen et al. | |
| 2005/0065073 A1* | 3/2005 | Wu et al. .................. | 514/10 |
| 2005/0143316 A1 | 6/2005 | Tu | |

FOREIGN PATENT DOCUMENTS

| | | |
|---|---|---|
| WO | WO 94/14436 A1 | 7/1994 |
| WO | WO 95/07696 | 3/1995 |
| WO | WO 95/09614 | 4/1995 |
| WO | WO 97/40028 | 10/1997 |
| WO | WO 98/17679 | 4/1998 |
| WO | WO 98/22496 | 5/1998 |
| WO | WO 98/40381 | 9/1998 |
| WO | WO 99/07734 | 2/1999 |
| WO | WO 99/37666 A1 | 7/1999 |
| WO | WO 00/09543 A2 | 2/2000 |
| WO | WO 00/56331 A1 | 9/2000 |
| WO | WO 00/59929 A | 10/2000 |
| WO | WO 01/16300 A2 | 3/2001 |
| WO | WO 01/49262 A1 | 7/2001 |
| WO | WO 01/74768 A2 | 10/2001 |
| WO | WO 02/08198 A2 | 1/2002 |
| WO | WO 02/08244 A2 | 1/2002 |

(Continued)

OTHER PUBLICATIONS

Vippagunta, et al. Advanced Drug Delivery Reviews 48 (2001) 3-26.*
Bodanszky, M., "Peptide Chemistry", 2$^{nd}$ Red. Ed., Springer-Verlag, Berlin, Germany (1993). Title Page and Table of Contents.

(Continued)

*Primary Examiner* — Shawquia Young
(74) *Attorney, Agent, or Firm* — Andrea Jo Kamage

(57) ABSTRACT

Inhibitors of HCV replication of formula (I)

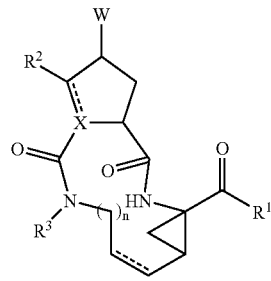

wherein
W is a heterocycle of formula

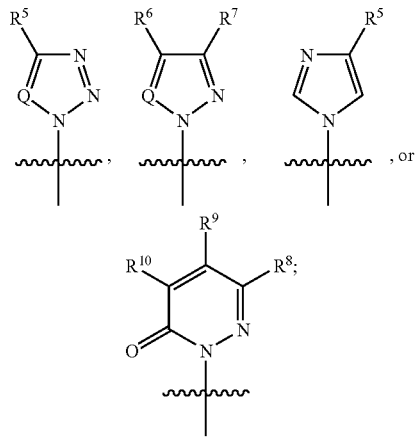

and the remaining variables are as defined in the specification.

12 Claims, No Drawings

FOREIGN PATENT DOCUMENTS

| WO | WO 02/08256 A2 | 1/2002 |
|---|---|---|
| WO | WO 02/18369 | 3/2002 |
| WO | WO 02/053557 A1 | 7/2002 |
| WO | WO 03/006490 A1 | 1/2003 |
| WO | WO 03/087092 A2 | 10/2003 |
| WO | WO 2004/072243 | 8/2004 |
| WO | WO 2005/010029 | 2/2005 |
| WO | WO 2005/073195 | 8/2005 |
| WO | WO 2005/073216 | 8/2005 |
| WO | WO 2007/014921 A1 | 2/2007 |
| WO | WO 2007/014922 A1 | 2/2007 |
| WO | WO 2007/014923 A1 | 2/2007 |
| WO | WO 2007/014924 A1 | 2/2007 |
| WO | WO 2007/014925 A1 | 2/2007 |
| WO | WO 2007/014926 A1 | 2/2007 |
| WO | WO 2007/014927 A1 | 2/2007 |

OTHER PUBLICATIONS

Dolby, L., et al., "Studies of the Synthesis of the B, C, and D Rings of Gibberellie Acid", in J. Org. Chem. 36 (1971) 1277-1285.

Elangovan, et al., "Sonogashira Coupling Reaction with Diminished Homocoupling", Organic Letters 2003 vol. 5 No. 11 p. 1841-1844.

Goodman and Gillman's "The Pharmacological Basis of Therapeutics" Eighth Edition, McGraw-Hill, Inc., Health Professions Division, p. 1-20 Title Page and Table of Conents.

Greene, "Protective Groups in Organic Chemistry", Wiley & Sons, NY (1999) "The Peptides: Analysis, Synthesis, Biology", vol. 9, Academic Press, NY (1987) Title Page and Table of Contents.

Huang, et al., "Olefin Metathesis-Active Ruthenium Complexes Bearing a Nucleophilic Carbene Ligand" J.Am. Chem. Soc. 1999 121, p. 2674-2678.

Kingsbury, J., "A Recyclable Ru-Based Metathesis Catalyst", et al., J.Am. Chem. Soc. 1999, 121, p. 791-799.

Krchnak, V. et al., "Polymer-Supported Mitsunobu Ether Formation and its Use in Combinatorial Chemistry", Tetrahedron Letters, vol. 36, No. 35, p. 6193-6195, 1995.

Krieger, N., et al., "Enhancement of Hepatitis C Virus RNA Replication by Cell Culture-Adaptive Mutations", Journal of Virology, May 2001, pp. 4614-4624.

Liu, Y., et al. "Use of a Fluorescence Plate Reader for Measuring Kinetic Parameters with Inner Filter Effect Correction", Analytical Biochemistry 267, pp. 331-335 (1999).

Lohmann, V., et al., "Replication of Subgenomic Hepatitis C Virus RNAs in a Hepatoma Cell Line", Science 285, 1999, pp. 110-113.

Miller, S., et al., "Application of Ring-Closing Metathesis to the Synthesis of Rigidified Amino Acids and Peptides", J.Am. Chem. Soc. 1996, 118, p. 9606-9614.

Mitsunobu, O., et al. "The Use of Diethyl Azodicarboxylate and Triphenylphospine in Synthesis and Transformation of Natural Products", Synthesis, Jan. 1-28, 1981.

Poliakov, "Expression and Purification of Recombinant Full-Length NS3 Protease-Helicase from a New Variant of Hepatitis C Virus", Prot Expression & Purification, 25, pp. 363-371, 2002.

Rano, T. et al., "Solid Phase Synthesis of Aryl Ethers via the Mitsunobu Reaction", Tetrahedron Letters, vol. 36, No. 22, pp. 3789-3792, 1995.

Richter, L. et al, "A Surprising Observation about Mitsunobu Reactions in Solid Phase Synthesis", Tetrahedron Letters, vol. 35, No. 27, p. 4705-4706, 1994.

Bredikhina, Z. et al., "Synthesis and Some Reactions of 4-Carboxy-2-Thilazolyhydrazones", Chem. Hyterocycl. Compd. (English translation) (1991), 427-433.

Briet, N. et al., "Synthesis of Novel Substituted Isoquinolones", Tetrahedron, 2002, p. 5761.

Cohen, E., et al., "Sulfamoyl Chloride, Sulfamides and Sulfimide", Organic Chemical Research Section, vol. 84, 1962, pp. 1994-2002.

Dewynter, G., et al., Synthesis of Chiral "Sulfahydantoins", Tetrahedron, vol. 49, No. 1, pp. 65-76.

Dickinson, R., et al. "Thromboxane Modulating Agenats. 3. IH-Imadozol-1-ylalkyl- and 3-pyridinylalkyl-substituted 3[2-[arylsulfonyl)amino]benzenepropanoc Receptor Antagonists", J. Med. Chem. 1997, 40 pp. 3442-3452.

Graf, R., "On Sulfamic Acid Chloride", Chemische Berichte, vol. 92, pp. 509-513 (1959).

Han, W., et al., "a-Ketoamides, a-Ketoesters and a-Diketones as HCV NS3 Protease Inhibitors", Bioorganic & Medicinal Chemistry Letters, vol. 10, No. 8, 2000, pp. 711-713.

Hirao et al., "Preparation of Optically Active 8,8'-Disubstituted 1,1' Bisoquinoline", Heterocycle, vol. 42(1), pp. 415-422 (1996).

Kloeck, J., et al. "An Improved Synthesis of Sulfamoyl Chlorides", J. Org. Chem., vol. 41, No. 25, 1976, pp. 4028-4029.

Landro et al., "Mechanistic Role of an NS4A Peptide Cofactor with the Truncated NS3 Protease of Hepatitis C Virus Elucidation of the NS4A Stimulatory Effect via Kinetic Analysis and Inhibitor Mapping", Biochemistry, vol. 36, pp. 9340-9348 (1997).

Rosenquist, et al., "Synthesis of Enantimerically Pure trans-3,4-Substituted Cyclopentanois by Enzymatic Resolution", Acta Chem. Scand. 46 (1992) 1127-1129.

Smith, E.M., et al., "Synthesis and Pharmacological Activity of Anagiotensin converting Enzyme Inhibitors: N-(Mercaptoacy)-4-substituted-(S)-Prolines", J. Med. Chem. (1988), 31, pp. 875-885.

Tozer, M., et al., "4-Chlorobenzyl Sulfonamide and Sulfamide Derivatives of Histamine Homologues: The Design of Potent Histamine H, Receptor Antagonists", Bioorganic & Medicinal Chemistry Letters 9 (1999) pp. 3103-3108.

Weiss, G., et al., "Production and Reactions of N-Monoalkyl Amidosulfonyl Chlorides", Liebigs, Ann. Chem, 729, pp. 40-51 (1969).

* cited by examiner

MACROCYLIC INHIBITORS OF HEPATITIS C VIRUS

CROSS REFERENCE TO RELATED APPLICATIONS

This application claims priority of the benefits of the filing of EP 051070712.0 filed Jul. 29, 2005 and PCT/EP2006/064818 filed Jul. 28, 2006. The complete disclosures of the aforementioned patent applications are hereby incorporated herein by reference for all purposes.

The present invention is concerned with macrocylic compounds having inhibitory activity on the replication of the hepatitis C virus (HCV). It further concerns compositions comprising thes 123qasdfgyhj>" /e compounds as active ingredients as well as processes for preparing these compounds proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168A and/or A156S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

WO04/072243 relates to macrocylic hepatitis C serine protease inhibitors; pharmaceutical compositions comprising the aforementioned compounds for administration to a subject suffering from HCV infection; and methods of treating an HCV infection in a subject by administering a pharmaceutical composition comprising the said compounds.

The present invention concerns HCV inhibitors which are superior in one or more of the following pharmacological related properties, i.e. potency, decreased cytotoxicity, improved pharmacokinetics, improved resistance profile, acceptable dosage and pill burden.

In addition, the compounds of the present invention have relatively low molecular weight and are easy to synthesize, starting from starting materials that are commercially available or readily available through art-known synthesis procedures.

The present invention concerns inhibitors of HCV replication, which can be represented by formula (I):

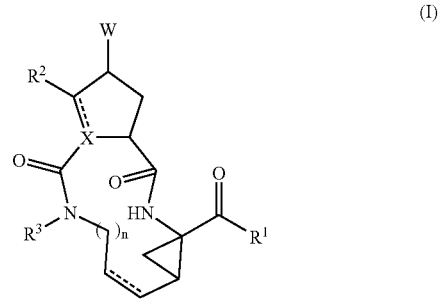

and the N-oxides, salts, and stereoisomers thereof, wherein
each dashed line (represented by - - - - -) represents an optional double bond;
X is N, CH and where X bears a double bond it is C;
$R^1$ is —$OR^{11}$, —NH—$SO_2R^{12}$;
$R^2$ is hydrogen, and where X is C or CH, $R^2$ may also be $C_{1-6}$alkyl;

$R^3$ is hydrogen, $C_{1-6}$alkyl, $C_{1-6}$alkoxyC$_{1-6}$alkyl, or $C_{3-7}$cycloalkyl;

n is 3, 4, 5, or 6;

W is a heterocycle of formula

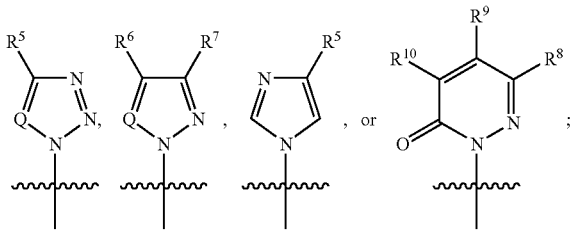

Q is N or $CR^4$;

$R^4$ is hydrogen; phenyl optionally substituted with $C_{1-6}$alkyl or with $C_{1-6}$alkoxy; thiazolyl optionally substituted with $C_{1-6}$alkyl; or pyridyl;

$R^5$ is phenyl optionally substituted with $C_{1-6}$alkyl or with $C_{1-6}$alkoxy; thiazolyl optionally substituted with $C_{1-6}$alkyl; or pyridyl;

one of $R^6$, $R^7$ is phenyl optionally substituted with $C_{1-6}$alkyl or with $C_{1-6}$alkoxy; thiazolyl optionally substituted with $C_{1-6}$alkyl; or pyridyl; while the other of $R^6$, $R^7$ is hydrogen; phenyl optionally substituted with $C_{1-6}$alkyl or with $C_{1-6}$alkoxy; thiazolyl optionally substituted with $C_{1-6}$alkyl; or pyridyl;

one of $R^8$, $R^9$, $R^{10}$ is phenyl optionally substituted with $C_{1-6}$alkyl or with $C_{1-6}$alkoxy; thiazolyl optionally substituted with $C_{1-6}$alkyl; or pyridyl; while the other two of $R^8$, $R^9$, $R^{10}$ independently are hydrogen; phenyl optionally substituted with $C_{1-6}$alkyl or with $C_{1-6}$alkoxy; thiazolyl optionally substituted with $C_{1-6}$alkyl; or pyridyl;

$R^{11}$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;

$R^{12}$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;

each aryl as a group or part of a group is phenyl, optionally substituted with one, two or three substituents selected from halo, hydroxy, nitro, cyano, carboxyl, $C_{1-6}$alkyl, $C_{1-6}$alkoxy, $C_{1-6}$alkoxyC$_{1-6}$alkyl, $C_{1-6}$alkylcarbonyl, amino, mono- or diC$_{1-6}$alkylamino, azido, mercapto, polyhaloC$_{1-6}$alkyl, polyhaloC$_{1-6}$alkoxy, $C_{3-7}$cycloalkyl, pyrrolidinyl, piperidinyl, piperazinyl, 4-C$_{1-6}$alkyl-piperazinyl, 4-C$_{1-6}$alkylcarbonyl-piperazinyl, morpholinyl; wherein the morpholinyl and piperidinyl groups may be optionally substituted with one or with two $C_{1-6}$alkyl radicals; and each Het as a group or part of a group is a 5 or 6 membered saturated, partially unsaturated or completely unsaturated heterocyclic ring containing 1 to 4 heteroatoms each independently selected from nitrogen, oxygen and sulfur, and being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxyC$_{1-6}$alkyl, $C_{1-6}$alkylcarbonyl, amino, mono- or diC$_{1-6}$alkylamino, azido, mercapto, polyhaloC$_{1-6}$alkyl, polyhaloC$_{1-6}$alkoxy, $C_{3-7}$cycloalkyl, pyrrolidinyl, piperidinyl, piperazinyl, 4-C$_{1-6}$alkyl-piperazinyl, 4-C$_{1-6}$alkylcarbonyl-piperazinyl, morpholinyl; wherein the morpholinyl and piperidinyl groups may be optionally substituted with one or with two $C_{1-6}$alkyl radicals.

The invention further relates to methods for the preparation of the compounds of formula (I), the N-oxides, addition salts, quaternary amines, metal complexes, and stereochemically isomeric forms thereof, their intermediates, and the use of the intermediates in the preparation of the compounds of formula (I).

The invention relates to the compounds of formula (I) per se, the N-oxides, addition salts, quaternary amines, metal complexes, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), or a N-oxide, addition salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I), or a N-oxide, addition salt, quaternary amine, metal complex, or stereochemically isomeric forms thereof.

As used in the foregoing and hereinafter, the following definitions apply unless otherwise noted.

The term halo is generic to fluoro, chloro, bromo and iodo.

The term "polyhaloC$_{1-6}$alkyl" as a group or part of a group, e.g. in polyhaloC$_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoroC$_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhaloC$_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-6}$alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$alkanediyl is $C_{1-4}$alkanediyl.

$C_{1-6}$alkoxy means $C_{1-6}$alkyloxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

The radical Het is a heterocycle as specified in this specification and claims. Examples of Het comprise, for example, pyrrolidinyl, piperidinyl, morpholinyl, thiomorpholinyl, piperazinyl, pyrrolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, and the like. Of interest amongst the Het radicals are those which are non-saturated, in particular those having an aromatic character. Of further interest are those Het radicals having one or two nitrogens.

Each of the Het radicals mentioned in this and the following paragraphs may be optionally substituted with the number and kind of substituents mentioned in the definitions of the compounds of formula (I) or any of the subgroups of compounds of formula (I). Some of the Het radicals mentioned in this and the following paragraphs may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Where Het is piperazinyl, it preferably is substituted in its 4-position by a substituent linked to the 4-nitrogen with a carbon atom, e.g. 4-$C_{1-6}$alkyl, 4-polyhalo$C_{1-6}$alkyl, $C_{1-6}$alkoxy$C_{1-6}$alkyl, $C_{1-6}$alkylcarbonyl, $C_{3-7}$cycloalkyl.

Interesting Het radicals comprise, for example pyrrolidinyl, piperidinyl, morpholinyl, thiomorpholinyl, piperazinyl, pyrrolyl, pyrazolyl, imidazolyl, oxazolyl, isoxazolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, phthalazinyl, benzimidazolyl, benzoxazolyl, benzisoxazolyl, benzothiazolyl, benzoxadiazolyl, benzothiadiazolyl, benzofuranyl, benzothienyl.

The Het radicals pyrrolidinyl, piperidinyl, morpholinyl, thiomorpholinyl, piperazinyl, 4-substituted piperazinyl preferably are linked via their nitrogen atom (i.e. 1-pyrrolidinyl, 1-piperidinyl, 4-thiomorpholinyl, 4-morpholinyl, 1-piperazinyl, 4-substituted 1-piperazinyl).

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), their prodrugs, N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo specifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes, and the intermediates used in the preparation thereof, the absolute stereochemical configuration was not experimentally determined.

A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolyzed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

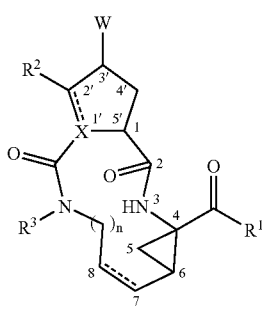

Asymmetric centers are present at positions 1, 4 and 6 of the macrocycle as well as at the carbon atom 3' in the 5-membered ring, carbon atom 2' when the $R^2$ substituent is $C_{1-6}$alkyl, and at carbon atom 1' when X is CH. Each of these asymmetric centers can occur in their R or S configuration.

The stereochemistry at position 1 preferably corresponds to that of an L-amino acid configuration, i.e. that of L-proline.

When X is CH, the 2 carbonyl groups substituted at positions 1' and 5' of the cyclopentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula

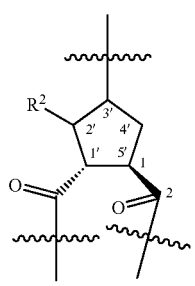

The compounds of formula (I) include a cyclopropyl group as represented in the structural fragment below:

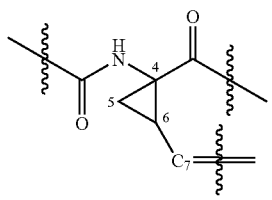

wherein $C_7$ represents the carbon at position 7 and carbons at position 4 and 6 are asymmetric carbon atoms of the cyclopropane ring.

Notwithstanding other possible asymmetric centers at other segments of the compounds of formula (I), the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

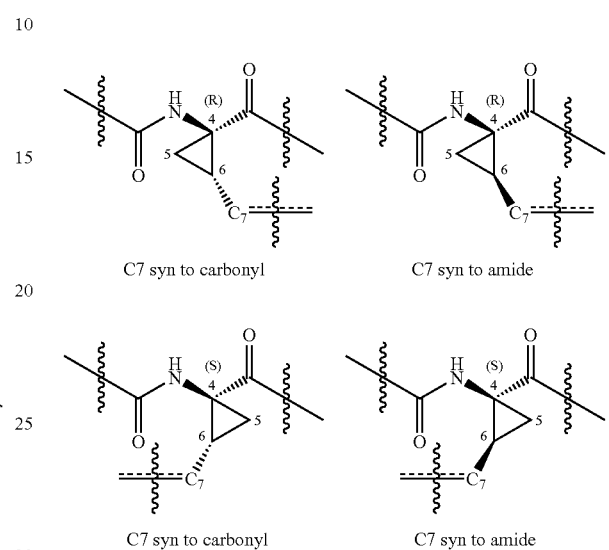

One embodiment concerns compounds of formula (I) wherein the carbon at position 7 is configured syn to the carbonyl. Another embodiment concerns compounds of formula (I) wherein the configuration at the carbon at position 4 is R. A specific subgroup of compounds of formula (I) are those wherein the carbon at position 7 is configured syn to the carbonyl and wherein the configuration at the carbon at position 4 is R.

The compounds of formula (I) may include a proline residue (when X is N) or a cyclopentyl or cyclopentenyl residue (when X is CH or C). Preferred are the compounds of formula (I) wherein the substituent at the 1 (or 5') position and the W substituent at position 3' are in a trans configuration. Of particular interest are the compounds of formula (I) wherein position 1 has the configuration corresponding to L-proline and the W substituent at position 3' is in a trans configuration in respect of position 1. Preferably the compounds of formula (I) have the stereochemistry as indicated in the structures of formulae (I-a) and (I-b) below:

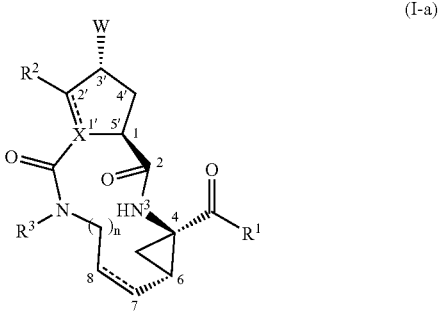

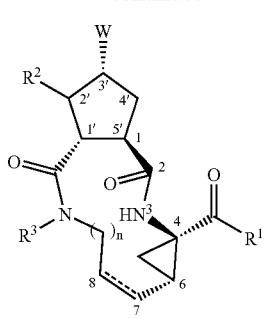

(I-b)

One embodiment of the present invention concerns compounds of formula (I) or of formula (I-a) or of any subgroup of compounds of formula (I), wherein one or more of the following conditions apply:
(a) $R^2$ is hydrogen;
(b) X is nitrogen;
(c) a double bond is present between carbon atoms 7 and 8.

One embodiment of the present invention concerns compounds of formula (I) or of formulae (I-a), (I-b), or of any subgroup of compounds of formula (I), wherein one or more of the following conditions apply:
(a) $R^2$ is hydrogen;
(b) X is CH;
(c) a double bond is present between carbon atoms 7 and 8.

Particular subgroups of compounds of formula (I) are those represented by the following structural formulae:

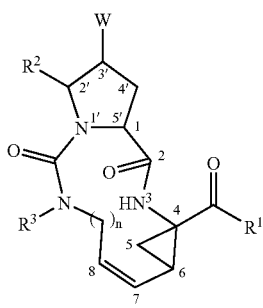

(I-c)

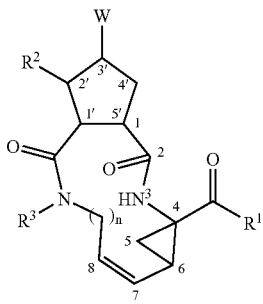

(I-d)

Amongst the compounds of formula (I-c) and (I-d), those having the stereochemical configuration of the compounds of formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

A double bond between carbon atoms 1' and 2' may be present in the compounds of formula (I), or in any subgroup of compounds of formula (I), as depicted in formula (I-e) below.

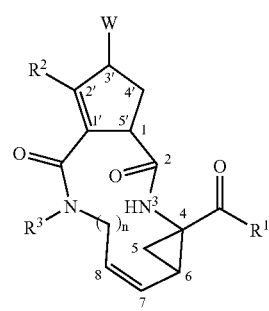

(I-e)

Yet another particular subgroup of compounds of formula (I) are those represented by the following structural formulae:

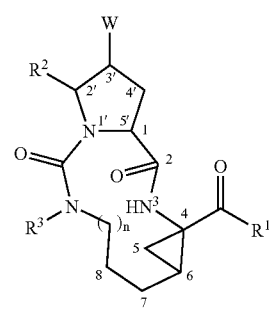

(I-f)

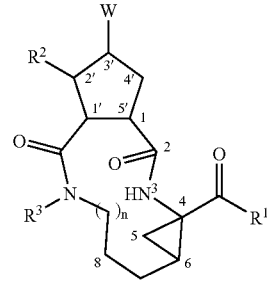

(I-g)

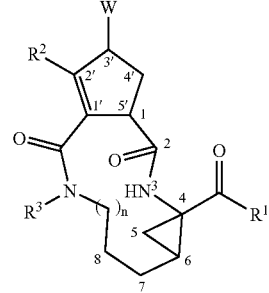

(I-h)

Amongst the compounds of formulae (I-f), (I-g) or (I-h), those having the stereochemical configuration of the compounds of formulae (I-a) and (I-b) are of particular interest.

In (I-a), (I-b), (I-c), (I-d), (I-e), (I-f), (I-g) and (I-h), where applicable, W, X, n, $R^1$, $R^2$, and $R^3$ are as specified in the definitions of the compounds of formula (I) or in any of the subgroups of compounds of formula (I) specified herein.

It is to be understood that the above defined subgroups of compounds of formulae (I-a), (I-b), (I-c), (I-d), (I-e), (I-f), (I-g) or (I-h), as well as any other subgroup defined herein, are meant to also comprise any prodrugs, N-oxides, addition salts, quaternary amines, metal complexes and stereochemically isomeric forms of such compounds.

When n is 2, the moiety —CH$_2$— bracketed by "n" corresponds to a ethanediyl in the compounds of formula (I) or in any subgroup of compounds of formula (I). When n is 3, the moiety —CH$_2$— bracketed by "n" corresponds to a propanediyl in the compounds of formula (I) or in any subgroup of compounds of formula (I). When n is 4, the moiety —CH$_2$— bracketed by "n" corresponds to a butanediyl in the compounds of formula (I) or in any subgroup of compounds of formula (I). When n is 5, the moiety —CH$_2$— bracketed by "n" corresponds to a pentanediyl in the compounds of formula (I) or in any subgroup of compounds of formula (I). When n is 6, the moiety —CH$_2$— bracketed by "n" corresponds to a hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein
(a) $R^1$ is —$OR^{11}$, in particular wherein $R^{11}$ is $C_{1-6}$alkyl, such as methyl, ethyl, or tert-butyl and most preferably where $R^{11}$ is hydrogen; or
(b) $R^1$ is —$NHS(=O)_2R^{12}$, in particular wherein $R^{12}$ is $C_{1-6}$alkyl, $C_3$-$C_7$cycloalkyl, or aryl, e.g. wherein $R^{12}$ is methyl, cyclopropyl, or phenyl; or
(c) $R^1$ is —$NHS(=O)_2R^{12}$, in particular wherein $R^{12}$ is $C_{3-7}$cycloalkyl substituted with $C_{1-6}$alkyl, preferably wherein $R^{12}$ is cyclopropyl, cyclobutyl, cyclopentyl, or cyclohexyl, any of which is substituted with $C_{1-4}$alkyl, i.e. with methyl, ethyl, propyl, isopropyl, butyl, tert-butyl, or isobutyl.

Further embodiments of the invention are compounds of formula (I) or any of the subgroups of compounds of formula (I) wherein $R^1$ is —$NHS(=O)_2R^{12}$, in particular wherein $R^{12}$ is cyclopropyl substituted with $C_{1-4}$alkyl, i.e. with methyl, ethyl, propyl, or isopropyl.

Further embodiments of the invention are compounds of formula (I) or any of the subgroups of compounds of formula (I) wherein $R^1$ is —$NHS(=O)_2R^{12}$, in particular wherein $R^{12}$ is 1-methylcyclopropyl.

Further embodiments of the invention are compounds of formula (I) or any of the subgroups of compounds of formula (I) wherein
(a) $R^2$ is hydrogen;
(b) $R^2$ is $C_{1-6}$alkyl, preferably methyl.

Embodiments of the invention are compounds of formula (I) or any of the subgroups of compounds of formula (I) wherein
(a) X is N, C (X being linked via a double bond) or CH (X being linked via a single bond) and $R^2$ is hydrogen;
(b) X is C (X being linked via a double bond) and $R^2$ is $C_{1-6}$alkyl, preferably methyl.

Further embodiments of the invention are compounds of formula (I) or any of the subgroups of compounds of formula (I) wherein
(a) $R^3$ is hydrogen;
(b) $R^3$ is $C_{1-6}$alkyl;
(d) $R^3$ is $C_{1-6}$alkoxy$C_{1-6}$alkyl or $C_{3-7}$cycloalkyl.

Preferred embodiments of the invention are compounds of formula (I) or any of the subgroups of compounds of formula (I) wherein $R^3$ is hydrogen, or $C_{1-6}$alkyl, more preferably hydrogen or methyl.

Embodiments of the invention are compounds of formula (I) or any of the subgroups of compounds of formula (I) wherein W is

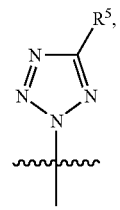

and $R^5$ is phenyl optionally substituted with $C_{1-6}$alkyl or with $C_{1-6}$alkoxy; thiazolyl optionally substituted with $C_{1-6}$alkyl; or pyridyl.

Embodiments of the invention are compounds of formula (I) or any of the subgroups of compounds of formula (I) wherein W is

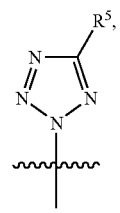

and $R^5$ is phenyl, 3-methoxyphenyl, 3,4-dimethoxyphenyl, 4-ethoxyphenyl, 4-propoxyphenyl, 4-butoxyphenyl, 2-pyridyl, 3-pyridyl, or 4-pyridyl.

Other subgroups of the compounds of formula (I) are those compounds of formula (I), or any subgroup of compounds of formula (I) specified herein, wherein W is

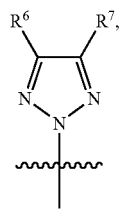

wherein $R^6$ is phenyl optionally substituted with $C_{1-6}$alkyl or with $C_{1-6}$alkoxy; thiazolyl optionally substituted with $C_{1-6}$alkyl; or pyridyl; and $R^7$ is hydrogen; phenyl optionally substituted with $C_{1-6}$alkyl or with $C_{1-6}$alkoxy; thiazolyl optionally substituted with $C_{1-6}$alkyl; or pyridyl.

Other subgroups of the compounds of formula (I) are those compounds of formula (I), or any subgroup of compounds of formula (I) specified herein, wherein W is

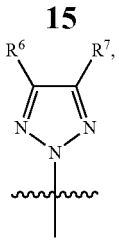

wherein R⁶ is phenyl, m-methoxyphenyl, 2-pyridyl, 3-pyridyl, or 2-thiazolyl; and R⁷ is phenyl, p-methoxyphenyl, or 4-ethoxyphenyl.

Embodiments of the invention are compounds of formula (I) or any of the subgroups of compounds of formula (I) wherein W is

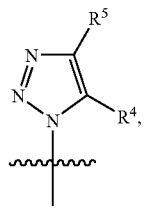

wherein R⁴ is hydrogen; phenyl optionally substituted with $C_{1-6}$alkyl or with $C_{1-6}$alkoxy; thiazolyl optionally substituted with $C_{1-6}$alkyl; or pyridyl; and R⁵ is phenyl optionally substituted with $C_{1-6}$alkyl or with $C_{1-6}$alkoxy; thiazolyl optionally substituted with $C_{1-6}$alkyl; or pyridyl.

Embodiments of the invention are compounds of formula (I) or any of the subgroups of compounds of formula (I) wherein W is

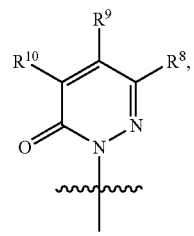

wherein one of R⁸, R⁹, R¹⁰ is phenyl optionally substituted with $C_{1-6}$alkyl or with $C_{1-6}$alkoxy; thiazolyl optionally substituted with $C_{1-6}$alkyl; or pyridyl; while the other two of R⁸, R⁹, R¹⁰ independently are hydrogen; phenyl optionally substituted with $C_{1-6}$alkyl or with $C_{1-6}$alkoxy; thiazolyl optionally substituted with $C_{1-6}$alkyl; or pyridyl.

Embodiments of the invention are compounds of formula (I) or any of the subgroups of compounds of formula (I) wherein W is

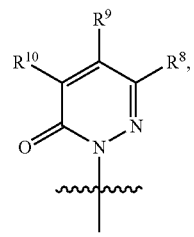

wherein R⁸ is hydrogen, 4-methoxyphenyl, or phenyl;

wherein R⁹ is hydrogen, phenyl, 4-methoxyphenyl, 3-pyridyl, or thiazol-2-yl;

wherein R¹⁰ is hydrogen, phenyl, 3-pyridyl, or thiazol-2-yl;

wherein each of the three substituents R⁸, R⁹, R¹⁰ independently is not hydrogen in the same molecule.

Embodiments of the invention are compounds of formula (I) or any of the subgroups of compounds of formula (I) wherein W is

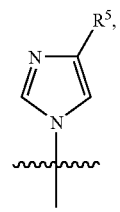

wherein R⁵ is phenyl optionally substituted with $C_{1-6}$alkyl or with $C_{1-6}$alkoxy; thiazolyl optionally substituted with $C_{1-6}$alkyl; or pyridyl.

Embodiments of the invention are compounds of formula (I) or any of the subgroups of compounds of formula (I) wherein W is

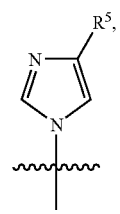

and R⁵ is phenyl, 3-methoxyphenyl, 3,4-dimethoxyphenyl, 4-ethoxyphenyl, 4-propoxyphenyl, 4-butoxyphenyl, 2-pyridyl, 3-pyridyl, 4-pyridyl, or thiazol-2-yl.

The compounds of formula (I) consist of three building blocks P1, P2, P3. Building block P1 further contains a P1' tail. The carbonyl group marked with an asterisk in compound (I-c) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (when R¹ is —NH—SO₂R¹²) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond.

The compounds of formula (I-j) can be prepared from the corresponding compounds of formula (I-I) by reducing the double bond in the macrocycle.

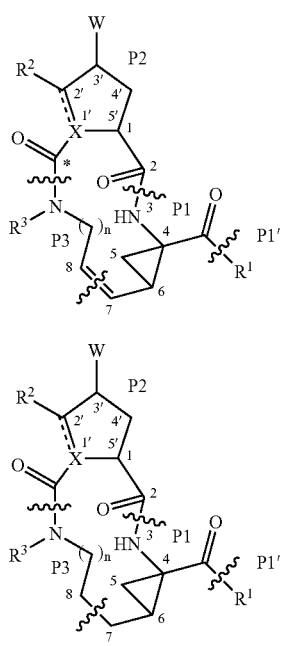

The synthesis procedures described hereinafter are meant to be applicable for as well the racemates, stereochemically pure intermediates or end products, or any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In one embodiment, compounds (I-i) are prepared by first forming the amide bonds and subsequent forming the double bond linkage between P3 and P1 with concomitant cyclization to the macrocycle.

In a preferred embodiment, compounds (I) wherein the bond between $C_7$ and $C_8$ is a double bond, which are compounds of formula (I-i), as defined above, may be prepared by as outlined in the following reaction scheme:

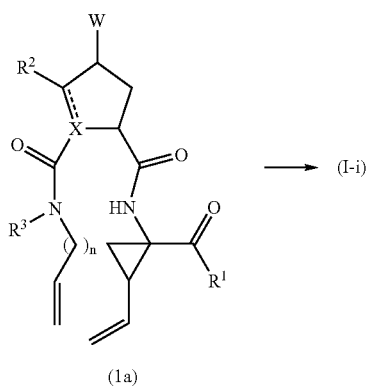

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. Benzylidene-bis(tricyclohexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)ruthenium(II) and 1,3-bis-(2,4,6-trimethylphenyl)-2-imidazolidinylidene)dichloro(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichloromethane, $CHCl_3$, 1,2-dichloroethane and the like. These reactions are conducted at increased temperatures under nitrogen atmosphere.

Compounds of formula (I) wherein the link between C7 and C8 in the macrocycle is a single bond, i.e. compounds of formula (I-i), can be prepared from the compounds of formula (I-j) by a reduction of the C7-C8 double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The $R^1$ group can be connected to the P1 building block at any stage of the synthesis, i.e. before or after the cyclization, or before or after the cyclization and reduction as described herein above. The compounds of formula (I) wherein $R^1$ represents $—NHSO_2R^{12}$, said compounds being represented by formula (I-k-1), can be prepared by linking the $R^1$ group to P1 by forming an amide bond between both moieties.

Similarly, the compounds of formula (I) wherein $R^1$ represents $—OR^{11}$, i.e. compounds (I-k-2), can be prepared by linking the $R^1$ group to P1 by forming an ester bond. In one embodiment, the $—OR^{11}$ groups are introduced in the last step of the synthesis of the compounds (I) as outlined in the following reaction schemes wherein G represents a group:

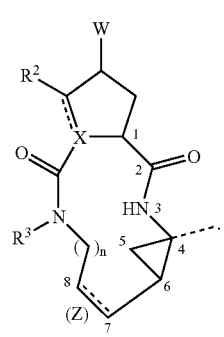

-continued

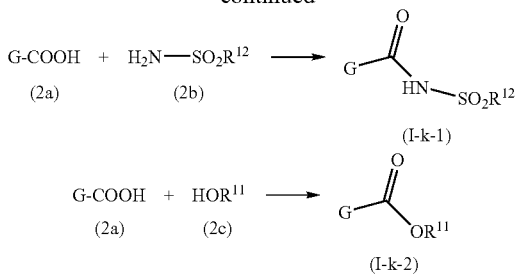

Intermediate (2a) can be coupled with the amine (2b) by an amide forming reaction such as any of the procedures for the formation of an amide bond described hereinafter. In particular, (2a) may be treated with a coupling agent, for example N,N'-carbonyl-diimidazole (CDI) or benzotriazol-1-yl-oxy-tris-pyrrolidinophosphonium hexafluorophosphate (commercially available as PyBOP®), in a solvent like THF, followed by reaction with the desired sulfonamide (2b) in the presence of a base such as 1,8-diazabicycle[5.4.0]undec-7-ene (DBU) or diisopropylethylamine. Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form, e.g. an acid chloride (G-CO—Cl) or a mixed acid anhydride (G-CO—O—CO—R, R being e.g. $C_{1-4}$alkyl or benzyl), and subsequently reacted with the alcohol (2c). The ester forming reactions preferably are conducted in the presence of a base such as an alkali metal carbonate or hydrogen carbonate, e.g. sodium or potassium hydrogen carbonate, or a tertiary amine such as the amines mentioned herein in relation to the amide forming reactions, in particular a trialkylamine, e.g. triethylamine. Solvents that can be used in the ester forming reactions comprise ethers such as THF; halogenated hydrocarbons such as dichloromethane, $CH_2Cl_2$; hydrocarbons such as toluene; polar aprotic solvents such as DMF, DMSO, DMA; and the like solvents.

The compounds of formula (I) wherein $R^3$ is hydrogen, said compounds being represented by (I-l), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

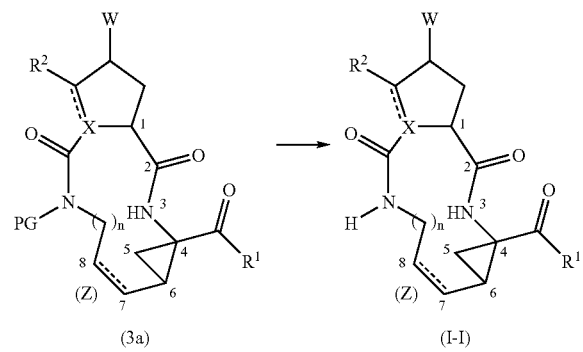

The starting materials (3a) in the above reaction can be prepared following the procedures for the preparation of compounds of formula (I), but using intermediates wherein the group $R^3$ is PG.

The compounds of formula (I) can also be prepared by reacting an intermediate (4a) with an heterocycle (4b) as outlined in the following reaction scheme wherein the various radicals have the meanings specified above:

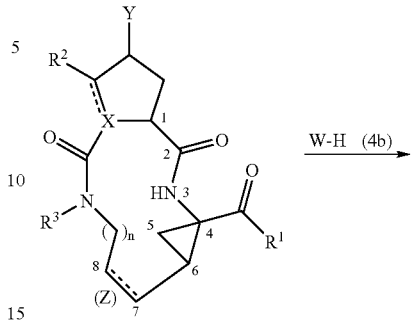

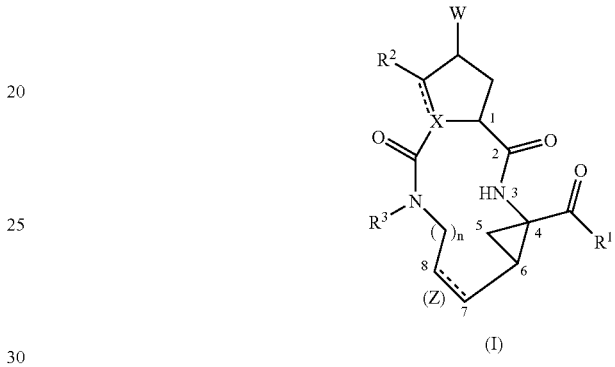

Y in (4a) represents hydroxy or a leaving group such as a halide, e.g. bromide or chloride, or an arylsulfonyl group, e.g. mesylate, triflate or tosylate and the like.

In one embodiment, the reaction of (4a) with (4b) is an O-arylation reaction and Y represents a leaving group. In particular, this reaction is conducted in the presence of a base, preferably a strong base, in a reaction-inert solvent, e.g. one of the solvents mentioned for the formation of an amide bond. In one embodiment, starting material (4a) is reacted with (4b) in the presence of a base which is strong enough to detract a hydrogen from the hydroxy group, for example an alkali of alkaline metal hydride such as LiH or NaH, or an alkali metal alkoxide such as sodium or potassium methoxide or ethoxide, potassium tert-butoxide, in a reaction inert solvent like a dipolar aprotic solvent, e.g. DMA, DMF and the like. The resulting alcoholate is reacted with the arylating agent (4b), wherein Y is a leaving group as mentioned above. The conversion of (4a) to (I) using this type of O-arylation reaction does not change the stereochemical configuration at the carbon bearing the Y or W group.

Alternatively, the reaction of (4a) with (4b) can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706). This reaction comprises treatment of intermediate (4a) wherein Y is hydroxyl with (4b), in the presence of triphenylphosphine and an activating agent such as a dialkyl azocarboxylate, e.g. diethyl azodicarboxylate (DEAD), diisopropyl azodicarboxylate (DIAD) or the like. The Mitsunobu reaction changes the stereochemical configuration at the carbon bearing the Y or W group.

The starting materials W—H (4b) can be prepared from known or commercially available products. Tetrazoles can be prepared by reacting commercially available nitrile compounds with sodium azide. Triazole derivatives can be prepared by reaction of an alkyne compound and trimethylsilyl azide. Useful alkyne compounds are available either commercially or can be prepared for instance according to the Sonogashira reaction i.e. reaction of a primary alkyne, an aryl halide and triethylamine in the presence of $PdCl_2(PPh)_3$ and CuI as described for example in A. Elangovan, Y.-H. Wang, T.-I. Ho, *Org. Lett.*, 2003, 5, 1841-1844. The W-substituent can also be modified when attached to the P2 building block, either before or after coupling of the P2 building block to the other building blocks P1 and P3.

Further alternatives for the coupling of the W group onto the P2 building block in the preparation of compounds of formula (I) has been extensively described in WO 2004/072243.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized, by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or ester formation.

The tail P1' can be bonded to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachlorophenyl, pentafluorophenyl, N-hydroxysuccinic imido and the like esters), the Woodward reagent K-method, the 1,1-carbonyldiimidazole (CDI or N,N'-carbonyldiimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo[5.4.0]undec-7-ene), or 4-DMAP. Further coupling agents are (benzotriazol-1-yloxy)tris-(dimethylamino) phosphonium hexafluorophosphate, either by itself or in the presence of 1-hydroxybenzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydro quino line (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methyl-morpholine, N-methylpyrrolidine, 4-DMAP or 1,8-diazabi-cycle[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:

1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and 7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared starting from intermediates (5a) which are reacted with an alkenamine (5b) in the presence of a carbonyl introducing agent as outlined in the following reaction scheme.

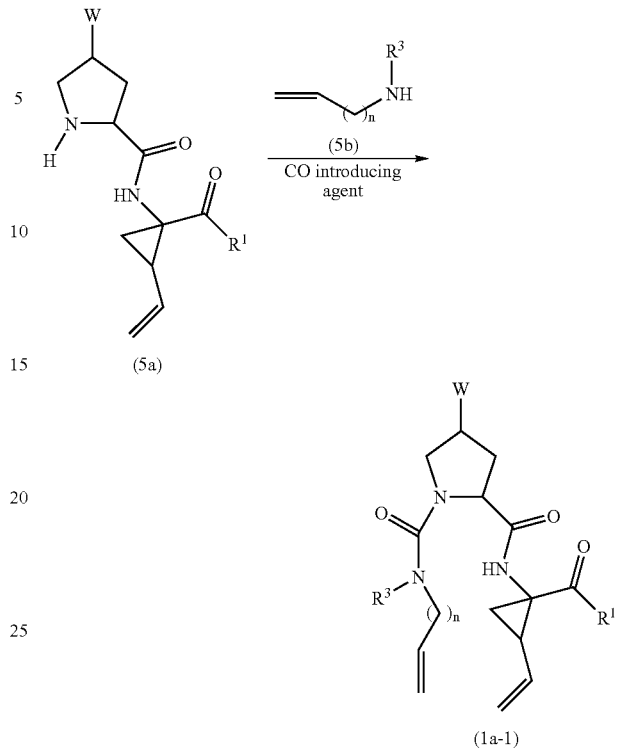

Carbonyl (CO) introducing agents include phosgene, or phosgene derivatives such as carbonyl diimidazole (CDI), and the like. In one embodiment (5a) is reacted with the CO introducing agent in the presence of a suitable base and a solvent, which can be the bases and solvents used in the amide forming reactions as described above. In a particular embodiment, the base is a hydrogencarbonate, e.g. $NaHCO_3$, or a tertiary amine such as triethylamine and the like, and the solvent is an ether or halogenated hydrocarbon, e.g. THF, $CH_2Cl_2$, $CHCl_3$, and the like. Thereafter, the amine (5b) is added thereby obtaining intermediates (1a-1) as in the above scheme. An alternative route using similar reaction conditions involves first reacting the CO introducing agent with the amine (5b) and then reacting the thus formed intermediate with (5a).

The intermediates (1a-1) can alternatively be prepared as follows:

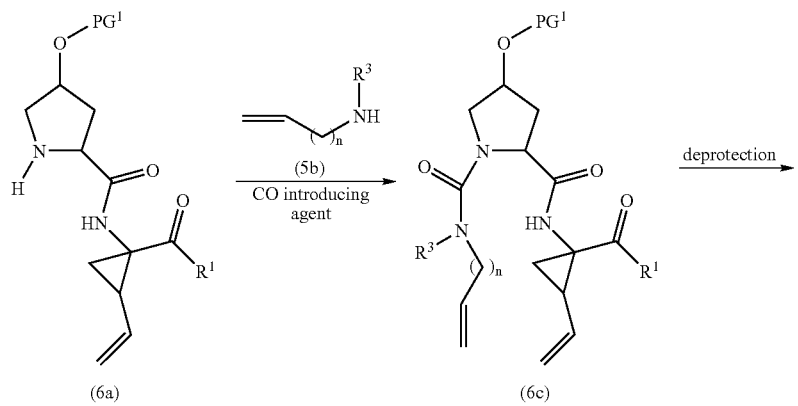

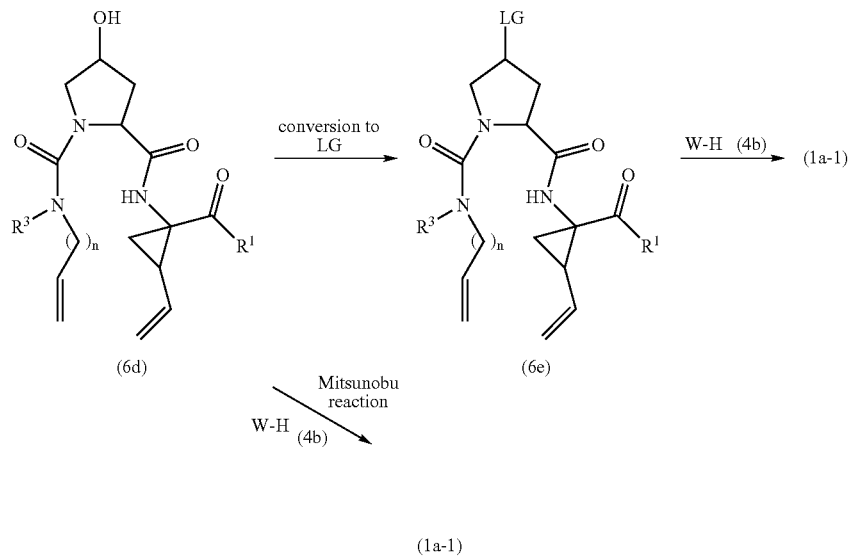

PG¹ is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG¹ is 4-nitrobenzoyl, with LiOH, in an aqueous medium comprising water and a water-soluble organic solvent such as an alkanol (methanol, ethanol) and THF.

Intermediates (6a) are reacted with (5b) in the presence of a carbonyl introducing agent, similar as described above, and this reaction yields intermediates (6c). These are deprotected, in particular using the reaction conditions mentioned above. The thus obtained intermediates (6d) can be converted directly to the target intermediates (1a-1) by a Mitsunobu reaction. The resulting alcohol in (6d) can also be converted to a leaving group LG resulting in intermediates (6e), which are reacted with intermediates (4b) as described above for the reaction of (4a) with (4b) and this reaction results in intermediates (1a-1). The alcohol functionality may be converted to a leaving group via art-known procedures, for example by reacting the alcohol with a halogenating reagent such as SOCl₂ or POCl₃, or by reacting the alcohol with a sulfonyl chloride such as tosyl, mesyl, pp.bromophenyl sulfonyl, trifluoromethylphenyl sulfonyl and the like.

The intermediates of formula (1a) wherein X is C, said intermediates being represented by formula (1a-2), may be prepared by an amide forming reaction starting from intermediates (7a) which are reacted with an amine (5b) as shown in the following reaction scheme, using reaction conditions for preparing amides such as those described above.

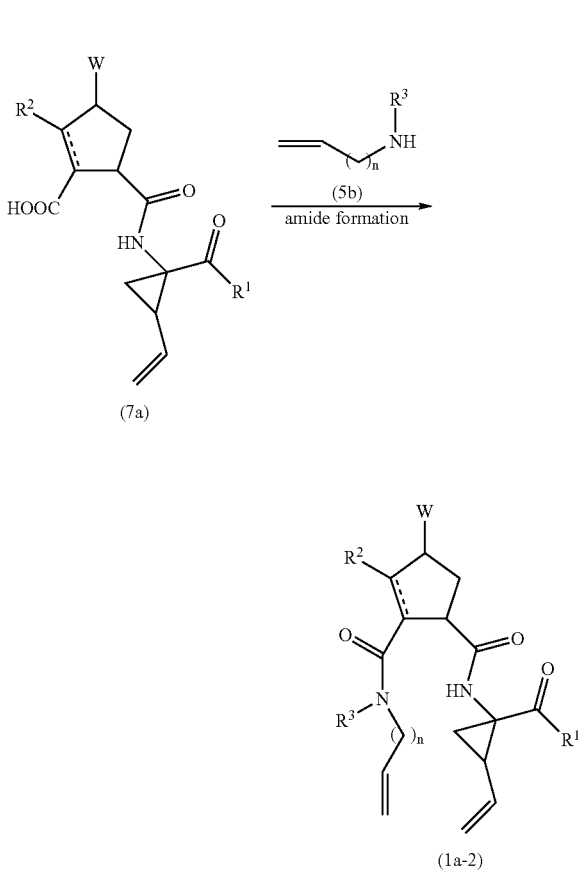

The intermediates (1a-1) can alternatively be prepared as follows:

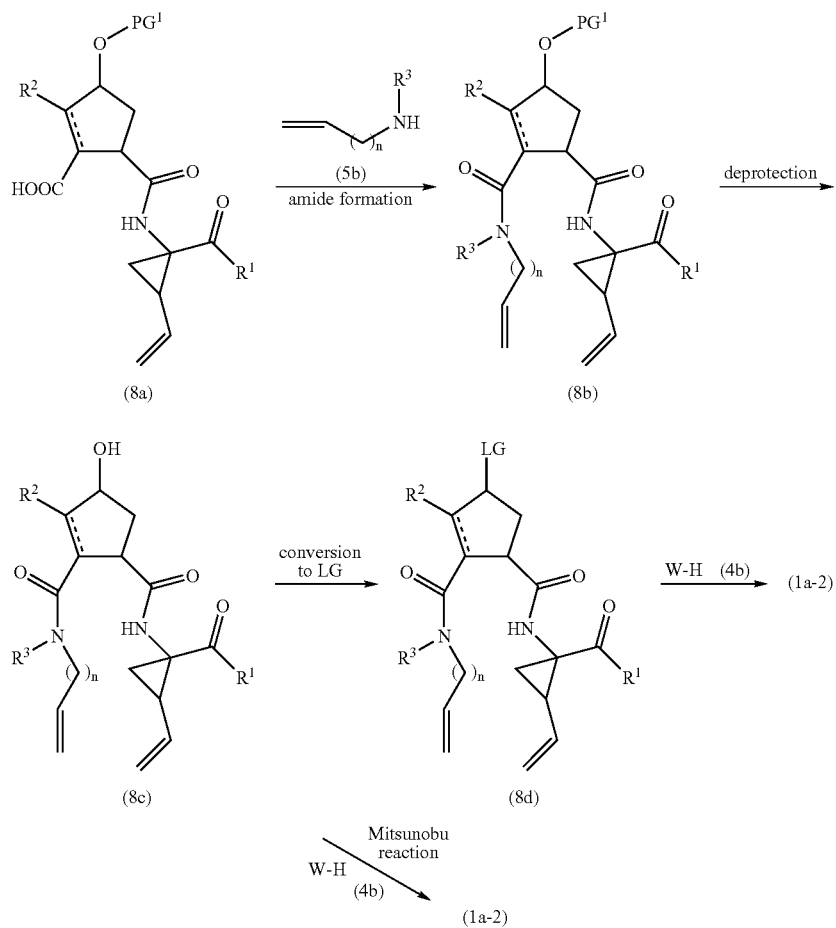

PG$^1$ is an O-protecting group as described above. The same reaction conditions as described above may be used: amide formation as described above, removal of PG$^1$ as in the description of the protecting groups, Mitsunobu reaction with (4b) or conversion of the alcohol functionality to a leaving group and introduction of W as in the reactions of (4a) with the reagents (4b).

The intermediates of formula (2a) may be prepared by first cyclizing the open amide (9a) to a macrocyclic ester (9b), which in turn is converted to (2a) as follows:

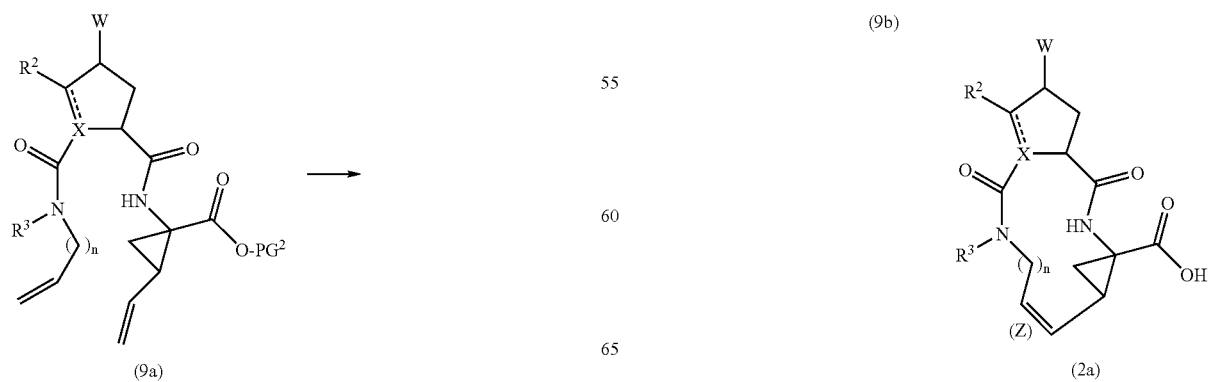

PG² is a carboxyl protecting group, e.g. one of the carboxyl protecting groups mentioned above, in particular a $C_{1-4}$alkyl or benzyl ester, e.g. a methyl, ethyl or t.butyl ester. The reaction of (9a) to (9b) is a metathesis reaction and is conducted as described above. The group PG² is removed following procedures also described above. Where PG¹ is a $C_{1-4}$alkyl ester, it is removed by alkaline hydrolysis, e.g. with NaOH or preferably LiOH, in an aqueous solvent, e.g. a $C_{1-4}$alkanol/water mixture. A benzyl group can be removed by catalytic hydrogenation.

In an alternative synthesis, intermediates (2a) can be prepared as follows:

weakly acidic conditions or PG¹ may be benzyl esters removable with strong acid or by catalytic hydrogenation, in the latter two cases PG¹ e.g. is a benzoic ester such as a 4-nitrobenzoic ester.

First, intermediates (10a) are cyclized to the macrocyclic esters (10b), the latter are deprotected by removal of the PG¹ group to (10c), which are reacted with intermediates (4b) to intermediates (10e), either directly via a Mitsunobu reaction, or by introducing a LG group and subsequent substitution with W—H. Removal of the carboxyl protecting group PG² in (10e) yields (2a). The cyclization, deprotection of PG¹ and PG², conversion to a leaving group LG and the coupling with (4b) are as described above.

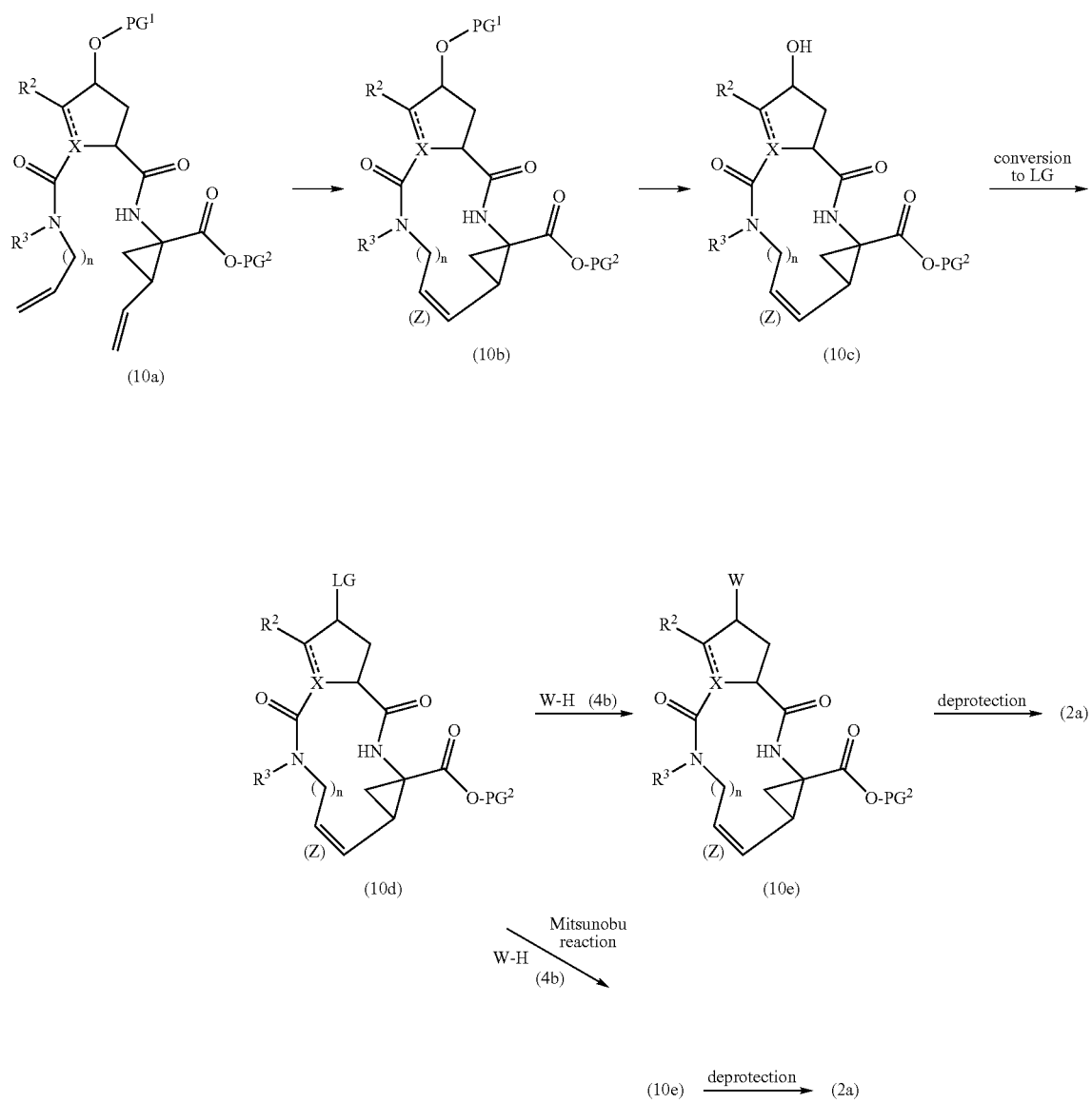

The PG¹ group is selected such that it is selectively cleavable towards PG². PG² may be e.g. methyl or ethyl esters, which can be removed by treatment with an alkali metal hydroxide in an aqueous medium, in which case PG¹ e.g. is t.butyl or benzyl. PG² may be t.butyl esters removable under Some of the R¹ groups can be introduced at any stage of the synthesis, either as the last step as described above, or earlier, before the macrocycle formation. In the following scheme the group R¹ being —NH—SO₂R¹² (which is as specified above) is introduced:

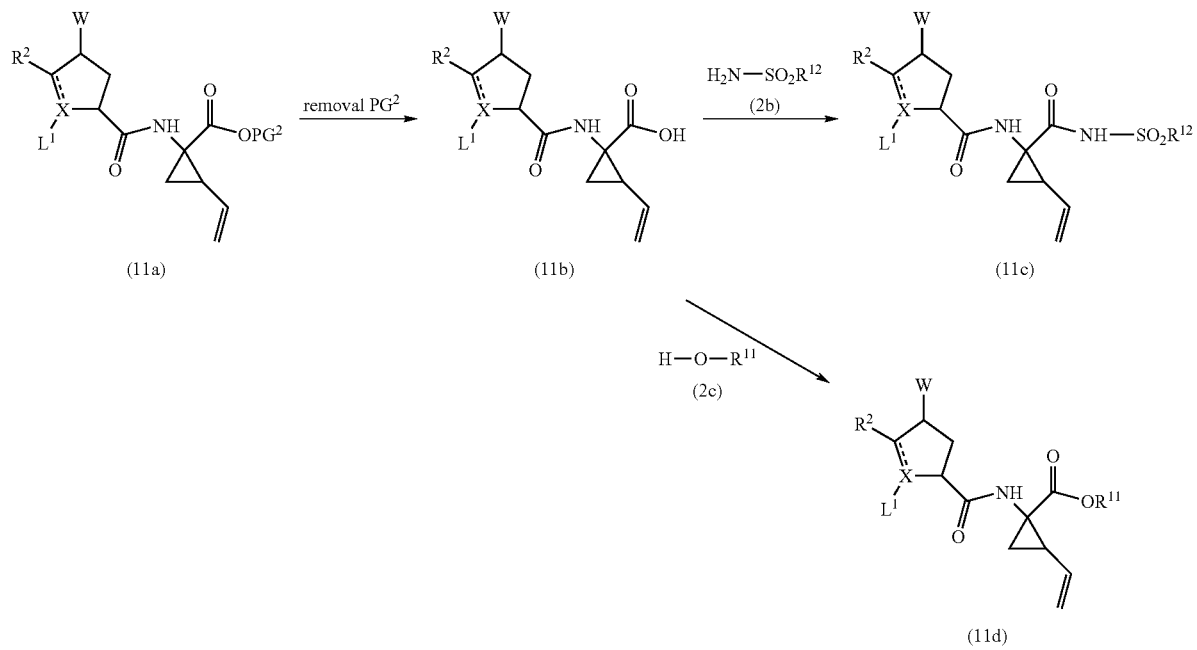

In the above scheme, $PG^2$ is as defined above and $L^1$ is a P3 group

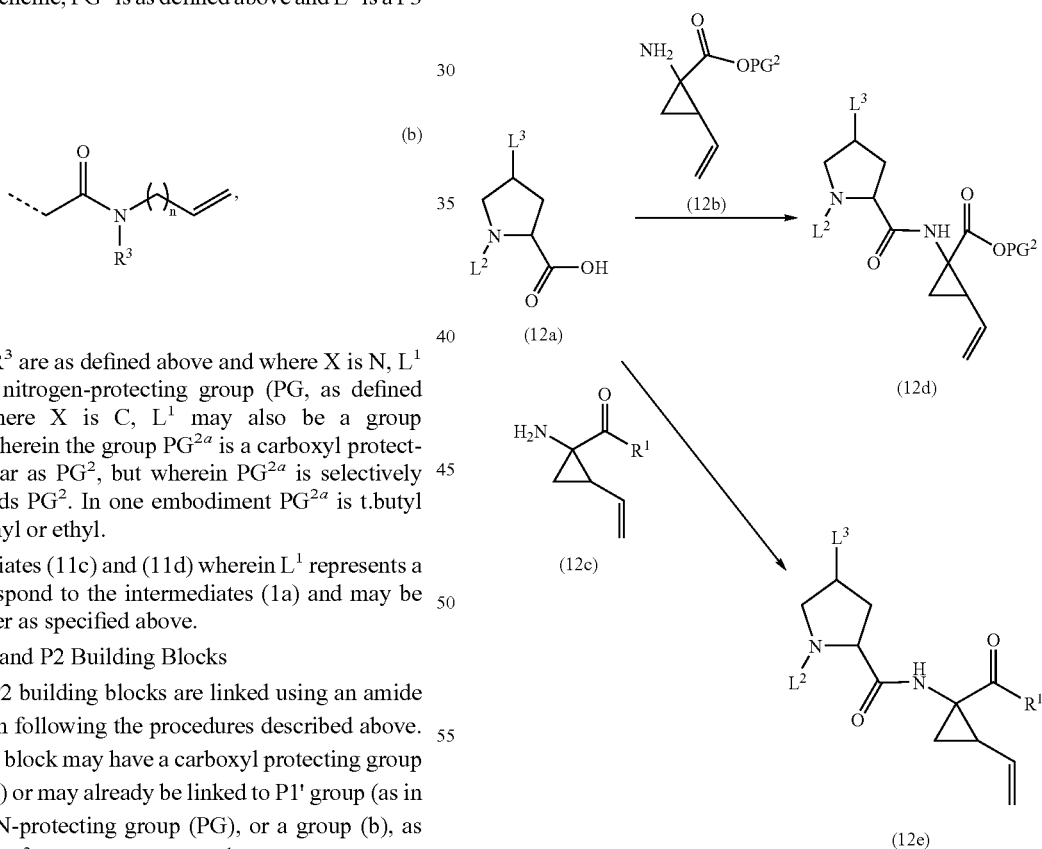

wherein n and $R^3$ are as defined above and where X is N, $L^1$ may also be a nitrogen-protecting group (PG, as defined above) and where X is C, $L^1$ may also be a group —$COOPG^{2a}$, wherein the group $PG^{2a}$ is a carboxyl protecting group similar as $PG^2$, but wherein $PG^{2a}$ is selectively cleavable towards $PG^2$. In one embodiment $PG^{2a}$ is t.butyl and $PG^2$ is methyl or ethyl.

The intermediates (11c) and (11d) wherein $L^1$ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group $PG^2$ (as in (12b)) or may already be linked to P1' group (as in (12c)). $L^2$ is a N-protecting group (PG), or a group (b), as specified above. $L^3$ is hydroxy, —$OPG^1$ or a group —W as specified above. Where in any of the following reaction schemes $L^3$ is hydroxy, prior to each reaction step, it may be protected as a group —$OPG^1$ and, if desired, subsequently deprotected back to a free hydroxy function. Similarly as described above, the hydroxy function may be converted to a group —W.

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter $L^2$ is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an amine H$_2$N—SO$_2$R$^{12}$ (2b) or with HOR$^{11}$ (2c) as described above, again yields the intermediates (12e), wherein —COR$^1$ are amide or ester groups. Where L$^2$ is a N-protecting group, it can be removed yielding intermediates (5a) or (6a). In one embodiment, PG in this reaction is a BOC group and PG$^2$ is methyl or ethyl. Where additionally L$^3$ is hydroxy, the starting material (12a) is Boc-L-hydroxyproline. In a particular embodiment, PG is BOC, PG$^2$ is methyl or ethyl and L$^3$ is —W.

In one embodiment, L$^2$ is a group (b) and these reactions involve coupling P1 to P2-P3, which results in the intermediates (1a-1) or (1a) mentioned above. In another embodiment, L$^2$ is a N-protecting group PG, which is as specified above, and the coupling reaction results in intermediates (12d-1) or (12e-1), from which the group PG can be removed, using reaction conditions mentioned above, obtaining intermediates (12-f) or respectively (12g), which encompass intermediates (5a) and (6a) as specified above:

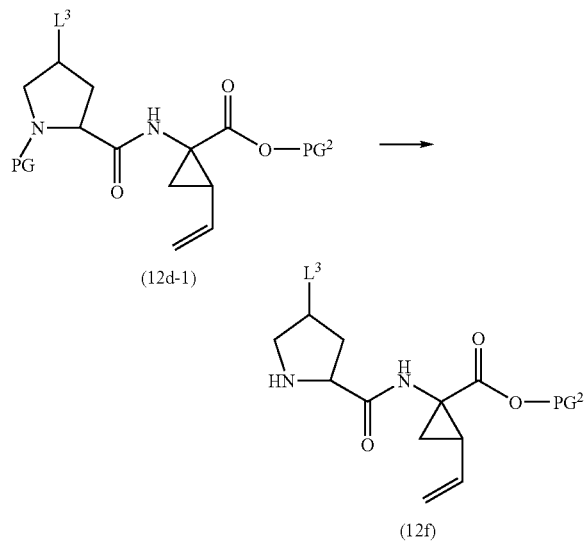

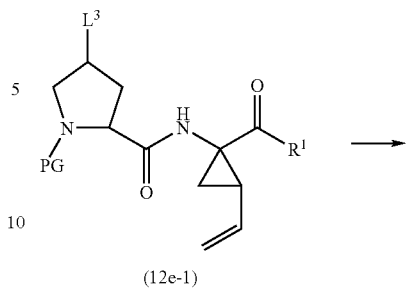

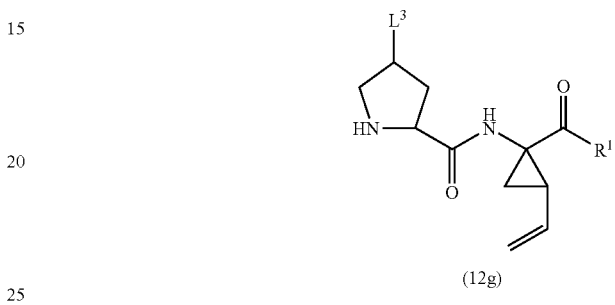

In one embodiment, the group L$^3$ in the above schemes represents a group —O—PG$^1$ which can be introduced on a starting material (12a) wherein L$^3$ is hydroxy. In this instance PG$^1$ is chosen such that it is selectively cleavable towards group L$^2$ being PG.

In a similar way, P2 building blocks wherein X is C, which are cyclopentane or cyclopentene derivatives, can be linked to P1 building blocks as outlined in the following scheme wherein R$^1$, R$^2$, L$^3$, PG$^2$ and PG$^{2a}$ are carboxyl protecting groups. PG$^{2a}$ typically is chosen such that it is selectively cleavable towards group PG$^2$. Removal of the PG$^{2a}$ group in (13c) yields intermediates (7a) or (8a), which can be reacted with (5b) as described above.

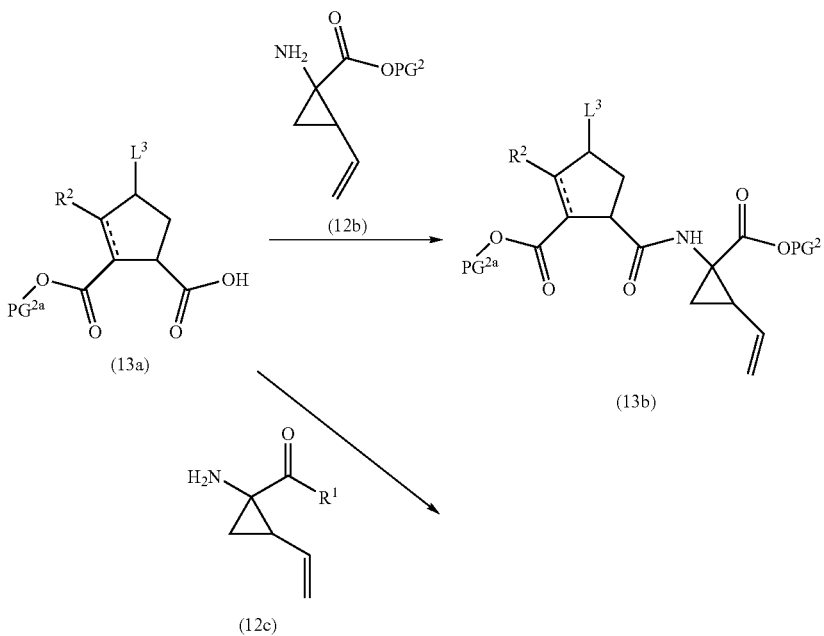

-continued

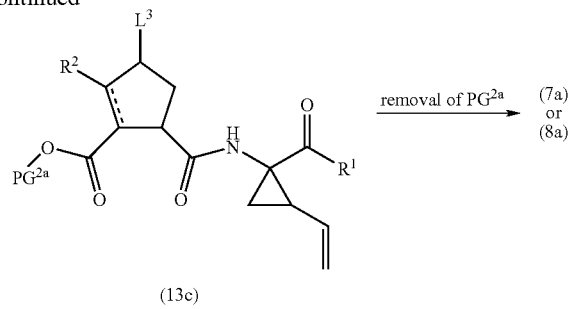

In one particular embodiment, where X is C, $R^2$ is H, and where X and the carbon bearing $R^2$ are linked by a single bond (P2 being a cyclopentane moiety), $PG^{2a}$ and $L^3$ taken together form a bond and the P2 building block is represented by formula:

(c) 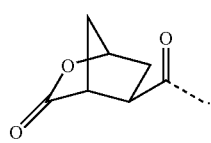

Bicyclic acid (14a) is reacted with (12b) or (12c) similar as described above to (14b) and (14c) respectively, wherein the lactone is opened giving intermediates (14c) and (14e). The lactones can be opened using ester hydrolysis procedures, for example using basic conditions such as an alkali metal hydroxide, e.g. NaOH, KOH, in particular LiOH.

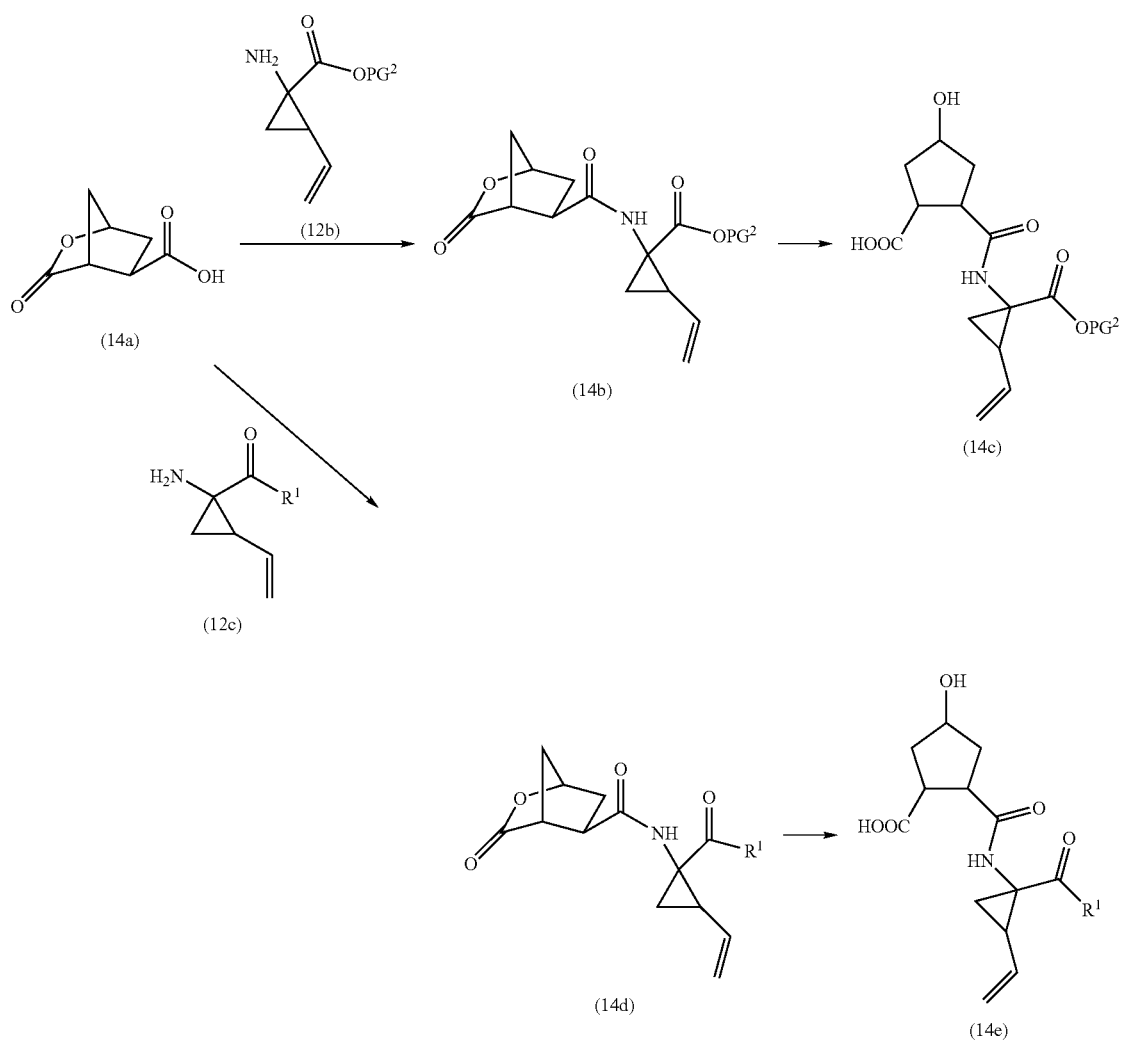

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using a carbamate forming reaction following the procedures described above for the coupling of (5a) or (6a) with (5b). A general procedure for coupling P2 blocks having a pyrrolidine moiety is represented in the following reaction scheme wherein $L^3$ is as specified above and $L^4$ is a group —O—$PG^2$, a group

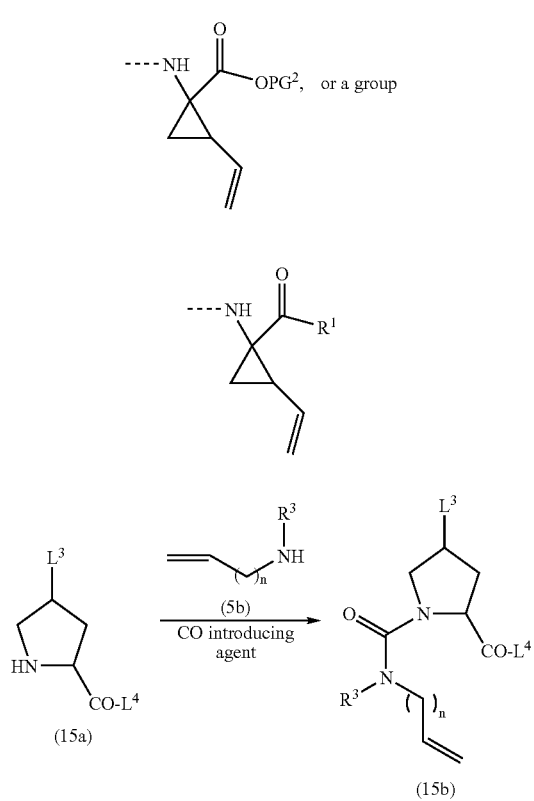

In one embodiment $L^4$ in (15a) is a group —$OPG^2$, the $PG^2$ group may be removed and the resulting acid coupled with cyclopropyl amino acids (12a) or (12b), yielding intermediates (12d) or (12e) wherein $L^2$ is a radical (d) or (e).

A general procedure for coupling P3 blocks with a P2 block or a with a P2-P1 block wherein the P2 is a cyclopentane or cyclopentene is shown in the following scheme.

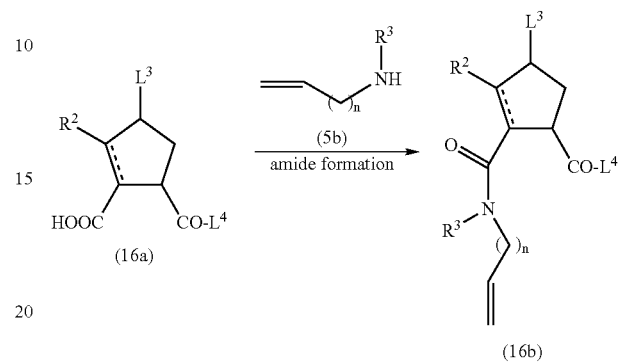

The reactions in the above two schemes are conducted using the same procedures as described above for the reactions of (5a), (7a) or (8a) with (5b) and in particular the above reactions wherein $L^4$ is a group (d) or (e) correspond to the reactions of (5a), (7a) or (8a) with (5b), described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group —W.

P2 building blocks containing a pyrrolidine moiety can be derived from commercially available hydroxy proline.

The preparation of P2 building blocks that contain a cyclopentane ring may be performed as shown in the scheme below.

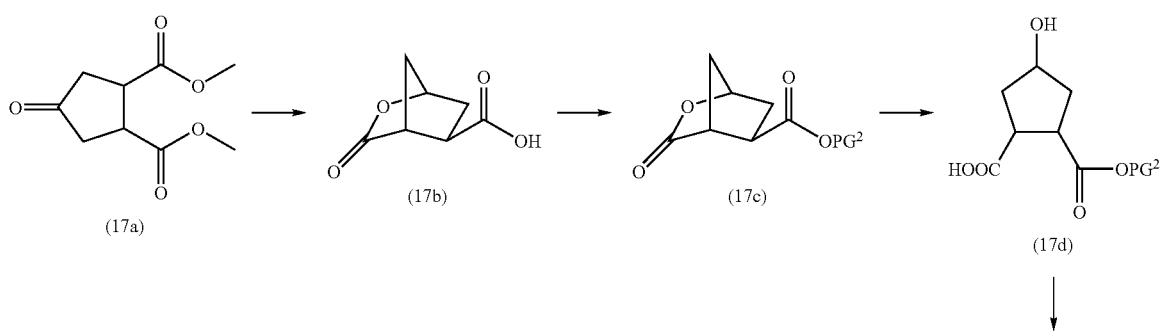

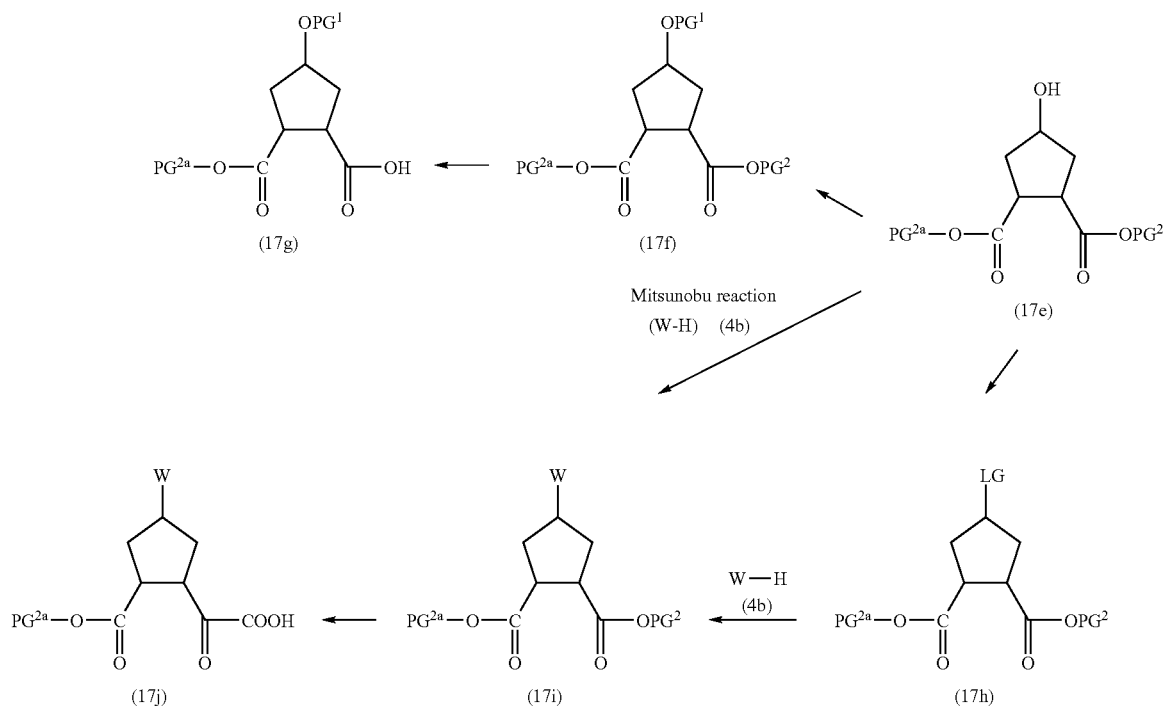

The bicyclic acid (17b) can be prepared, for example, from 3,4-bis(methoxycarbonyl)cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group $PG^2$, which is as specified above, thus providing bicyclic ester (17c). The group $PG^2$ in particular is acid-labile such as a t.butyl group and is introduced e.g. by treatment with isobutene in the presence of a Lewis acid or with di-tert-butyl dicarbonate in the presence of a base such as a tertiary amine like dimethylamino-pyridine or triethylamine in a solvent like dichloromethane. Lactone opening of (17c) using reaction conditions described above, in particular with lithium hydroxide, yields the acid (17d), which can be used further in coupling reactions with P1 building blocks. The free acid in (17d) may also be protected, preferably with an acid protecting group $PG^{2a}$ that is selectively cleavable towards $PG^2$, and the hydroxy function may be converted to a group —$OPG^1$ or to a group —W. Intermediates (17e) can be converted to intermediates (17i) by introducing a group W using a Mitsunobu reaction. Alternatively, the alcohol functionality in (17e) can be converted to a leaving group and the resulting intermediates (17h) can be reacted with a reagent (4b) to intermediates (17i). The products obtained upon removal of the group $PG^2$ are intermediates (17g) and (17j) which correspond to intermediates (13a) or (16a) specified above.

Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the OH function by using specific reagents in the reactions introducing $OPG^1$ or W that invert the stereochemistry, such as, e.g. by applying a Mitsunobu reaction.

In one embodiment, the intermediates (17d) are coupled to P1 blocks (12b) or (12c), which coupling reactions correspond to the coupling of (13a) or (16a) with the same P1 blocks, using the same conditions. Subsequent introduction of a —W-substituent as described above, followed by removal of the acid protection group $PG^2$ yields intermediates (8a-1), which are a subclass of the intermediates (7a), or part of the intermediates (16a). The reaction products of the $PG^2$ removal can be further coupled to a P3 building block. In one embodiment $PG^2$ in (17d) is t.butyl which can be removed under acidic conditions, e.g. with trifluoroacetic acid.

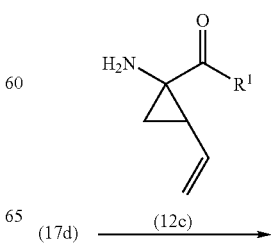

(17d)  (12c) →

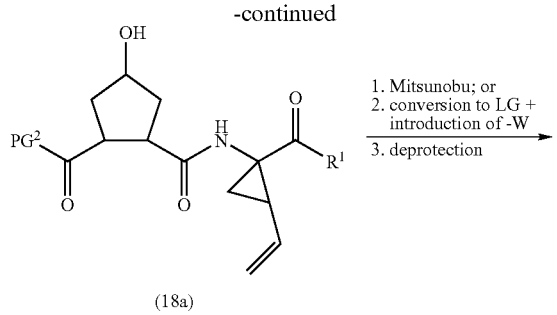

(18a)

1. Mitsunobu; or
2. conversion to LG + introduction of -W
3. deprotection

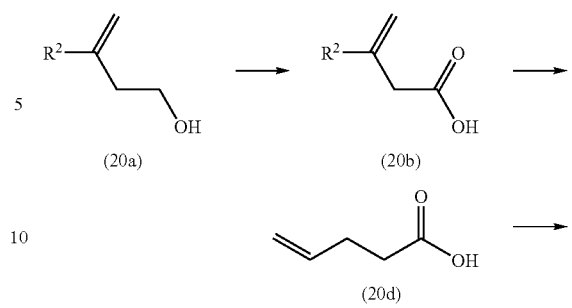

(20a)  (20b)

(20d)

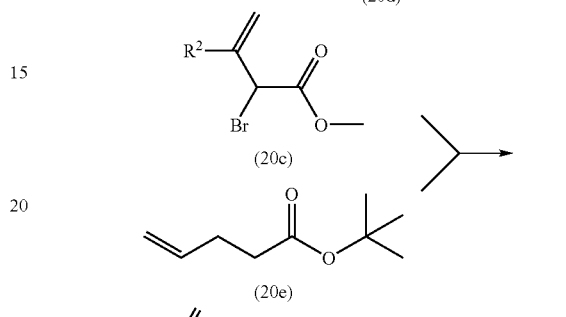

(20c)

(20e)

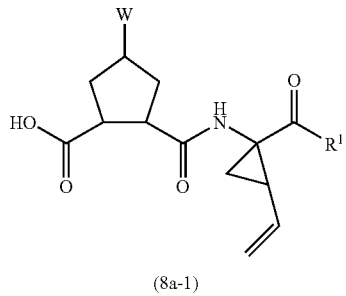

(8a-1)

An unsaturated P2 building block, i.e. a cyclopentene ring, may be prepared as illustrated in the scheme below.

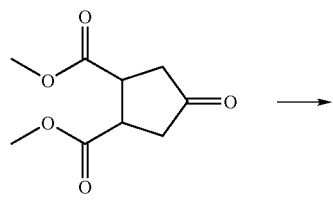

(17a)

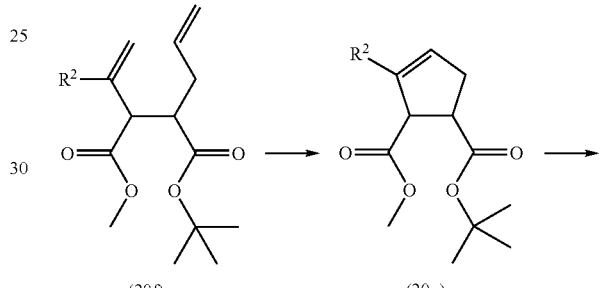

(20f)  (20g)

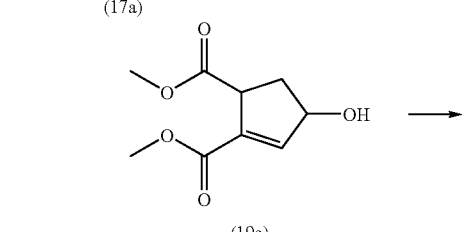

(19a)

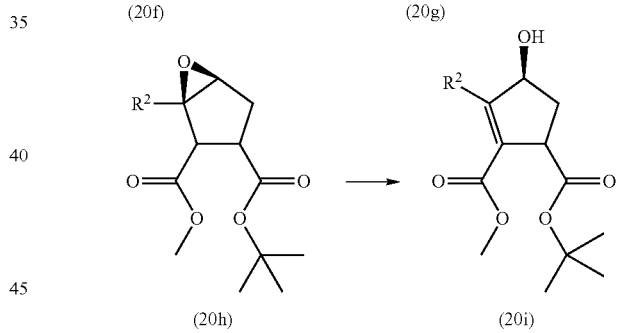

(20h)  (20i)

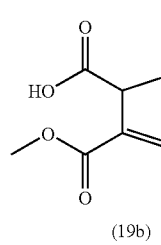

(19b)

A bromination-elimination reaction of 3,4-bis(methoxycarbonyl)cyclopentanone (17a) as described by Dolby et al. in J. Org. Chem. 36 (1971) 1277-1285 followed by reduction of the keto functionality with a reducing agent like sodium borohydride provides the cyclopentenol (19a). Selective ester hydrolysis using for example lithium hydroxide in a solvent like a mixture of dioxane and water, provides the hydroxy substituted monoester cyclopentenol (19b).

An unsaturated P2 building block wherein $R^2$ can also be other than hydrogen, may be prepared as shown in the scheme below.

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treatment with di-tert-butyl dicarbonate in the presence of a base like dimethylaminopyridine. Intermediate (20e) is treated with a base such as lithium diisopropyl amide in a solvent like tetrahydrofuran, and reacted with (20c) to give the alkenyl diester (20f). Cyclization of (20f) by an olefin metathesis reaction, performed as described above, provides cyclopentene derivative (20g). Stereoselective epoxidation of (20g) can be carried out using the Jacobsen asymmetric epoxidation method to obtain epoxide (20h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to the corresponding acid, which subsequently is coupled to a P1 building block.

The —W group can be introduced on the pyrrolidine, cyclopentane or cyclopentene rings at any convenient stage of the synthesis of the compounds according to the present invention. One approach is to first introduce the —W group to the said rings and subsequently add the other desired building blocks, i.e. P1 (optionally with the P1' tail) and P3, followed by the macrocycle formation. Another approach is to couple the building blocks P2, bearing no —W substituent, with each P1 and P3, and to add the —W group either before or after the macrocycle formation. In the latter procedure, the P2 moieties have a hydroxy group, which may be protected by a hydroxy protecting group $PG^1$.

W-groups can be introduced on building blocks P2 by converting hydroxy substituted intermediates (21a) to (21b) and reacting the latter with intermediates (4b) as described above for the synthesis of (I) starting from (4a). These reactions are represented in the schemes below, wherein PG is a N-protecting group, and $L^5$ and $L^{5a}$ independently from one another, represent hydrogen or a carboxyl protecting group $PG^2$ or $PG^{2a}$. The groups PG, $PG^2$ and $PG^{2a}$ are as specified above. Where the groups $L^5$ and $L^{5a}$ are $PG^2$ or $PG^{2a}$, they are chosen such that each group is selectively cleavable towards the other. For example, one of $L^5$ and $L^{5a}$ may be a methyl or ethyl group and the other a benzyl or t.butyl group.

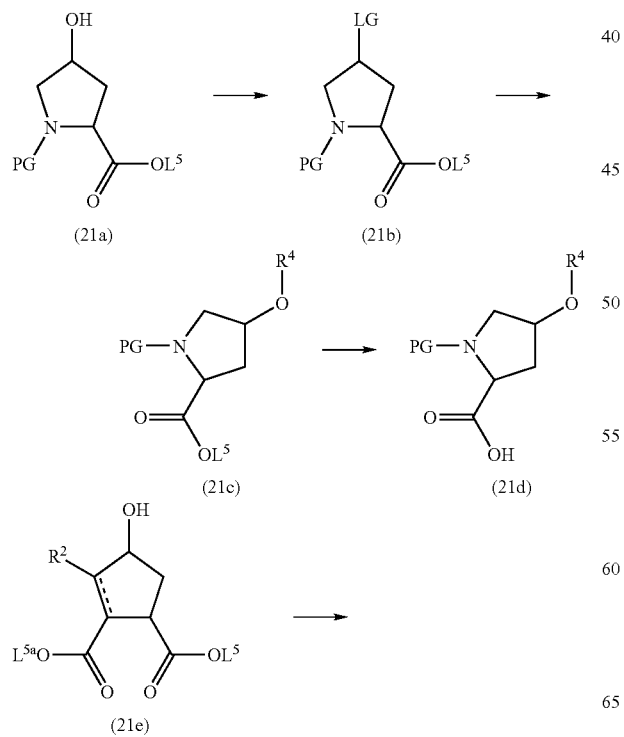

-continued

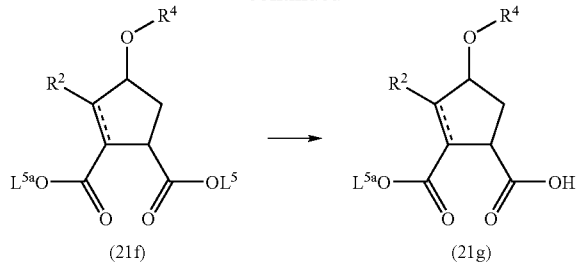

In one embodiment the group PG is BOC, $L^5$ is hydrogen and the starting material (21a) is commercially available BOC-hydroxyproline, or any other stereoisomeric form thereof, e.g. BOC-L-hydroxyproline, in particular the trans isomer of the latter. Where $L^5$ in (21c) is a carboxyl protecting group, it may be removed following procedures described above to (21d). In one embodiment PG in (21c) is Boc and $L^5$ is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide such as NaOH, in particular with LiOH. In another embodiment, hydroxy substituted cyclopentane or cyclopentene analogs (21e) are converted to (21f), which, where $L^5$ and $L^{5a}$ are $PG^2$ or $PG^{2a}$, may be converted to the corresponding acids (21g) by removal of the group $PG^2$. Removal of $PG^{2a}$ in (21f) leads to similar intermediates.

Synthesis of P1 Building Blocks

The cyclopropane amino acid used in the preparation of the P1 fragment is commercially available or can be prepared using art-known procedures.

In particular the amino-vinyl-cyclopropyl ethyl ester (12b) may be obtained according to the procedure described in WO 00/09543 or as illustrated in the following scheme, wherein $PG^2$ is a carboxyl protecting group as specified above:

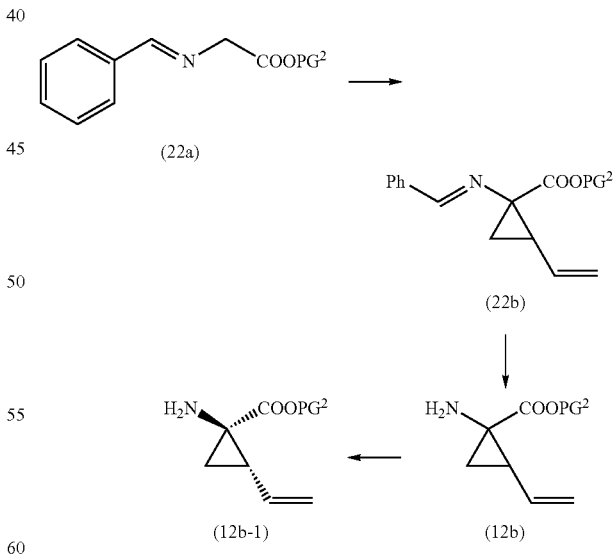

Treatment of commercially available or easily obtainable imine (22a) with 1,4-dihalo-butene in presence of a base produces (22b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate proline derivatives as described above.

P1 building blocks for the preparation of compounds according to general formula (I) wherein $R^1$ is —$OR^{11}$ or —NH—$SO_2R^{12}$ can be prepared by reacting amino acids (23a) with the appropriate alcohol or amine respectively under standard conditions for ester or amide formation. Cyclopropyl amino acids (23a) are prepared by introducing a N-protecting group PG, and removal of $PG^2$ and the amino acids (23a) are converted to the amides (12c-1) or esters (12c-2), which are subgroups of the intermediates (12c), as outlined in the following reaction scheme, wherein PG is as specified above.

Synthesis of the P3 Building Blocks

The P3 building blocks are available commercially or can be prepared according to methodologies known to the skilled in the art. One of these methodologies is shown in the scheme below and uses monoacylated amines, such as trifluoroacetamide or a Boc-protected amine.

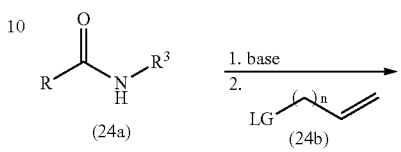

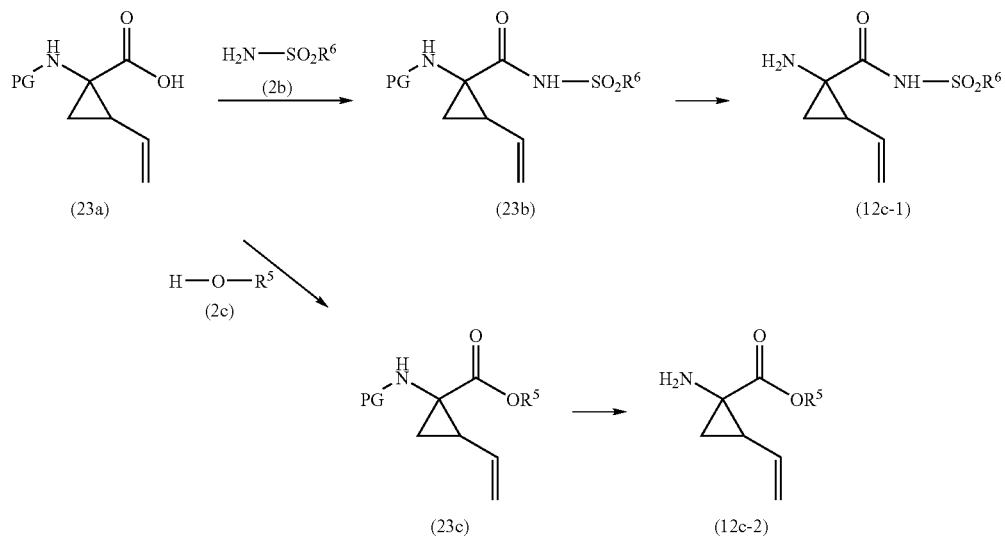

The reaction of (23a) with amine (2b) is an amide forming procedure. The similar reaction with (2c) is an ester forming reaction. Both can be performed following the procedures described above. This reaction yields intermediates (23b) or (23c) from which the amino protecting group is removed by standard methods such as those described above. This in turn results in the desired intermediate (12c-1). Starting materials (23a) may be prepared from the above mentioned intermediates (12b) by first introducing a N-protecting group PG and subsequent removal of the group $PG^2$.

In one embodiment the reaction of (23a) with (2b) is done by treatment of the amino acid with a coupling agent, for example N,N'-carbonyl-diimidazole (CDI) or the like, in a solvent like THF followed by reaction with (2b) in the presence of a base such as 1,8-diazabicyclo[5.4.0]undec-7-ene (DBU). Alternatively the amino acid can be treated with (2b) in the presence of a base like diisopropylethylamine followed by treatment with a coupling agent such as benzotriazole-1-yl-oxy-tris-pyrrolidino-phosphonium hexafluorophosphate (commercially available as PyBOP®) to effect the introduction of the sulfonamide group.

Intermediates (12c-1) or (12c-2) in turn may be coupled to the appropriate proline, cyclopentane or cyclopentene derivatives as described above.

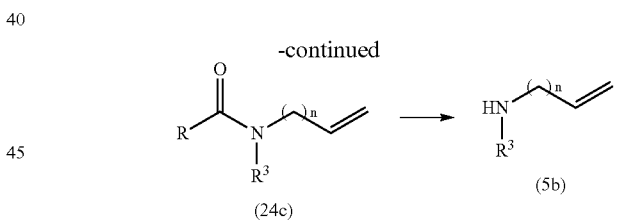

In the above scheme, R together with the CO group forms a N-protecting group, in particular R is t-butoxy, trifluoromethyl; $R^3$ and n are as defined above and LG is a leaving group, in particular halogen, e.g. chloro or bromo.

The monoacylated amines (24a) are treated with a strong base such as sodium hydride and are subsequently reacted with a reagent LG-$C_{5-8}$alkenyl (24b), in particular halo$C_{5-8}$alkenyl, to form the corresponding protected amines (24c). Deprotection of (24c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoromethyl, removal of the R group is accomplished with a base, e.g. sodium hydroxide.

The following scheme illustrates yet another method for preparing a P3 building block, namely a Gabriel synthesis of primary $C_{5-8}$alkenylamines, which can be carried out by the treatment of a phthalimide (25a) with a base, such as NaOH or KOH, and with (24b), which is as specified above, followed by hydrolysis of the intermediate N-alkenyl imide to generate a primary C$_{5-8}$alkenylamine (5b-1).

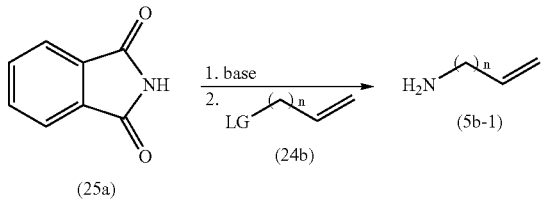

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover are active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavorable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624, which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from an HCV polymerase inhibitor, an HCV protease inhibitor, an inhibitor of another target in the HCV life cycle, and immunomodulatory agent, an antiviral agent, and combinations thereof.

HCV polymerase inhibitors include, but are not limited to, NM283 (valopicitabine), R803, JTK-109, JTK-003, HCV-371, HCV-086, HCV-796 and R-1479.

Inhibitors of HCV proteases (NS2-NS3 inhibitors and NS3-NS4A inhibitors) include, but are not limited to, the compounds of WO02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO98/17679, WO00/056331 (Vertex); WO 98/22496 (Roche); WO 99/07734, (Boehringer Ingelheim), WO 2005/073216, WO 2005073195 (Medivir) and structurally similar agents.

Inhibitors of other targets in the HCV life cycle, including NS3 helicase; metalloprotease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, but are not limited to; natural and recombinant interferon isoform compounds, including α-interferon, β-interferon, γ-interferon, ω-Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride; propagermanium; tetrachlorodecaoxide; ampligen; IMP-321; KRN-7000; antibodies, such as civacir, XTL-6865 and the like; and prophylactic and therapeutic vaccines such as InnoVac C, HCV E1E2/MF59 and the like.

Other antiviral agents include, but are not limited to, ribavirin, amantadine, viramidine, nitazoxanide; telbivudine; NOV-205; taribavirin; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO97/40028, WO98/40381, WO00/56331, and mycophenolic acid and derivatives thereof, and including, but not limited to VX-950, merimepodib (VX-497), VX-148, and/or VX-944); or combinations of any of the above.

Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In still another aspect there are provided combinations of a compound of formula (I) as specified herein and an anti-HIV compound. The latter preferably are those HIV inhibitors that have a positive effect on drug metabolism and/or pharmacokinetics that improve bioavailability. An example of such an HIV inhibitor is ritonavir.

As such, the present invention further provides a combination comprising (a) an HCV NS3/4a protease inhibitor of formula (I) or a pharmaceutically acceptable salt thereof; and (b) ritonavir or a pharmaceutically acceptable salt thereof.

The compound ritonavir, and pharmaceutically acceptable salts thereof, and methods for its preparation are described in WO94/14436. For preferred dosage forms of ritonavir, see U.S. Pat. No. 6,037,157, and the documents cited therein: U.S. Pat. No. 5,484,801, U.S. Ser. No. 08/402,690, and WO95/07696 and WO95/09614. Ritonavir has the following formula:

In a further embodiment, the combination comprising (a) an HCV NS3/4a protease inhibitor of formula (I) or a pharmaceutically acceptable salt thereof; and (b) ritonavir or a pharmaceutically acceptable salt thereof; further comprises an additional anti-HCV compound selected from the compounds as described herein.

In one embodiment of the present invention there is provided a process for preparing a combination as described herein, comprising the step of combining an HCV NS3/4a protease inhibitor of formula (I) or a pharmaceutically acceptable salt thereof, and ritonavir or a pharmaceutically acceptable salt thereof. An alternative embodiment of this invention provides a process wherein the combination comprises one or more additional agent as described herein.

The combinations of the present invention may be used as medicaments. Said use as a medicine or method of treatment comprises the systemic administration to HCV-infected subjects of an amount effective to combat the conditions associated with HCV and other pathogenic flavi- and pestiviruses. Consequently, the combinations of the present invention can be used in the manufacture of a medicament useful for treating, preventing or combating infection or disease associated with HCV infection in a mammal, in particular for treating conditions associated with HCV and other pathogenic flavi- and pestiviruses.

In one embodiment of the present invention there is provided a pharmaceutical composition comprising a combination according to any one of the embodiments described herein and a pharmaceutically acceptable excipient. In particular, the present invention provides a pharmaceutical composition comprising (a) a therapeutically effective amount of an HCV NS3/4a protease inhibitor of the formula (I) or a pharmaceutically acceptable salt thereof, (b) a therapeutically effective amount of ritonavir or a pharmaceutically acceptable salt thereof, and (c) a pharmaceutically acceptable excipient. Optionally, the pharmaceutical composition further comprises an additional agent selected from an HCV polymerase inhibitor, an HCV protease inhibitor, an inhibitor of another target in the HCV life cycle, and immunomodulatory agent, an antiviral agent, and combinations thereof.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product which results, directly or indirectly, from the combination of the specified ingredients.

In one embodiment the combinations provided herein may also be formulated as a combined preparation for simulta-

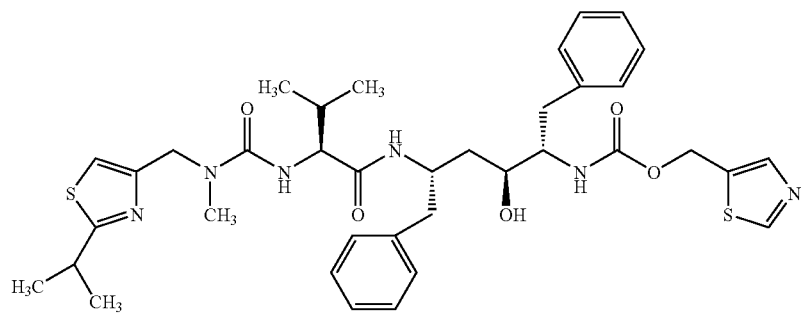

neous, separate or sequential use in HIV therapy. In such a case, the compound of general formula (I) or any subgroup thereof, is formulated in a pharmaceutical composition containing other pharmaceutically acceptable excipients, and ritonavir is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering" is to be interpreted accordingly. In a preferred embodiment, the separate dosage forms are administered about simultaneously.

In one embodiment, the combination of the present invention contains an amount of ritonavir, or a pharmaceutically acceptable salt thereof, which is sufficient to clinically improve the bioavailability of the HCV NS3/4a protease inhibitor of formula (I) relative to the bioavailability when said HCV NS3/4a protease inhibitor of formula (I) is administered alone.

In another embodiment, the combination of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

A further embodiment relates to a method for improving the bioavailability of a HCV NS3/4a protease inhibitor comprising administering to an individual in need of such improvement a combination as defined herein, comprising a therapeutically effective amount of each component of said combination.

In a further embodiment, the invention relates to the use of ritonavir or a pharmaceutically acceptable salt thereof, as an improver of at least one of the pharmacokinetic variables of a HCV NS3/4a protease inhibitor of formula (I) selected from $t_{1/2}$, $C_{min}$, $C_{max}$, $C_{ss}$, AUC at 12 hours, or AUC at 24 hours; with the proviso that said use is not practiced in the human or animal body.

The term "individual" as used herein refers to an animal, preferably a mammal, most preferably a human, who has been the object of treatment, observation or experiment.

Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$ represents the highest (maximum) concentration measured during the dosing interval. AUC is defined as the area under the plasma concentration-time curve for a defined period of time.

The combinations of this invention can be administered to humans in dosage ranges specific for each component comprised in said combinations. The components comprised in said combinations can be administered together or separately. The NS3/4a protease inhibitors of formula (I) or any sub-group thereof, and ritonavir or a pharmaceutically acceptable salt or ester thereof, may have dosage levels of the order of 0.02 to 5.0 grams-per-day.

When the HCV NS3/4a protease inhibitor of formula (I) and ritonavir are administered in combination, the weight ratio of the HCV NS3/4a protease inhibitor of formula (I) to ritonavir is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HCV NS3/4a protease inhibitors of formula (I) to ritonavir ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HCV NS3/4a protease inhibitors of formula (I) is equal to or greater than that of ritonavir, wherein the weight ratio of the HCV NS3/4a protease inhibitor of formula (I) to ritonavir is suitably in the range of from about 1:1 to about 15:1, typically from about 1:1 to about 10:1, and more typically from about 1:1 to about 8:1. Also useful are weight ratios of the HCV NS3/4a protease inhibitor of formula (I) to ritonavir ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) ritonavir, would be the amount of the compound of formula (I) and the amount of ritonavir that when taken together have a combined effect that is therapeutically effective.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as one, two, three, four or more (sub-)doses at appropriate intervals throughout the day. Said (sub-)doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

According to one embodiment, the HCV NS3/4a protease inhibitor of formula (I) and ritonavir may be co-administered once or twice a day, preferably orally, wherein the amount of the compounds of formula (I) per dose is from about 1 to about 2500 mg, and the amount of ritonavir per dose is from 1 to about 2500 mg. In another embodiment, the amounts per dose for once or twice daily co-administration are from about 50 to about 1500 mg of the compound of formula (I) and from about 50 to about 1500 mg of ritonavir. In still another embodiment, the amounts per dose for once or twice daily co-administration are from about 100 to about 1000 mg of the compound of formula (I) and from about 100 to about 800 mg of ritonavir. In yet another embodiment, the amounts per dose for once or twice daily co-administration are from about 150 to about 800 mg of the compound of formula (I) and from about 100 to about 600 mg of ritonavir. In yet another embodiment, the amounts per dose for once or twice daily co-administration are from about 200 to about 600 mg of the compound of formula (I) and from about 100 to about 400 mg of ritonavir. In yet another embodiment, the amounts per dose for once or twice daily co-administration are from about 200 to about 600 mg of the compound of formula (I) and from about 20 to about 300 mg of ritonavir. In yet another embodiment, the amounts per dose for once or twice daily co-administration are from about 100 to about 400 mg of the compound of formula (I) and from about 40 to about 100 mg of ritonavir.

Exemplary combinations of the compound of formula (I) (mg)/ritonavir (mg) for once or twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the compound of formula (I) (mg)/ritonavir (mg) for once or twice daily dosage include 1200/400, 800/400, 600/400, 400/200, 600/200, 600/100, 500/100, 400/50, 300/50, and 200/50.

In one embodiment of the present invention there is provided an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, or a combination according to the invention combining an HCV NS3/4a protease inhibitor of formula (I) or a pharmaceutically acceptable salt thereof, and ritonavir or a pharmaceutically acceptable salt thereof, in an amount effective for use as a standard or reagent in a test or assay for determining the ability of potential pharmaceuticals to inhibit HCV NS3/4a protease, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

Example 1

Preparation of 17-(5-phenyltetrazol-2-yl)-13-methyl-2,14-dioxo-3,13,15-triazatricyclo[13.3.0.0$^{4,6}$]octadec-7-ene-4-carboxylic acid (9)

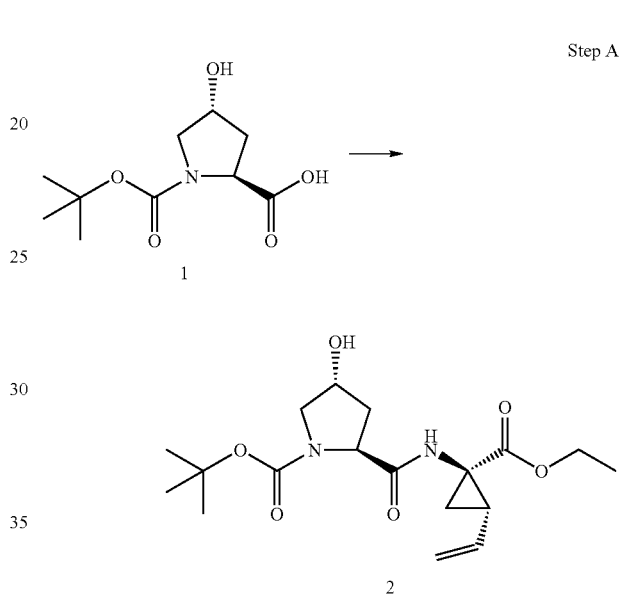

Step A

Boc-protected hydroxyproline 1 (4.0 g, 17.3 mmol), HATU (6.9 g, 18.2 mmol) and the 1-(amino)-2-(vinyl)cyclopropanecarboxylic acid ethyl ester (3.5 g, 18.3 mmol) were dissolved in DMF (60 mL) and cooled to 0° C. on ice-bath. Then, DIPEA (6.0 mL) was added. The ice-bath was removed and the mixture was left at ambient temperature for 12 h. Dichloromethane was then added and the organic phase was washed with aqueous sodium hydrogen carbonate, citric acid, water, brine and dried (Na$_2$SO$_4$). Purification by flash chromatography (gradient ether to ether/methanol, 93:7) gave 6.13 g (96%) of the target product 2 as an oil.

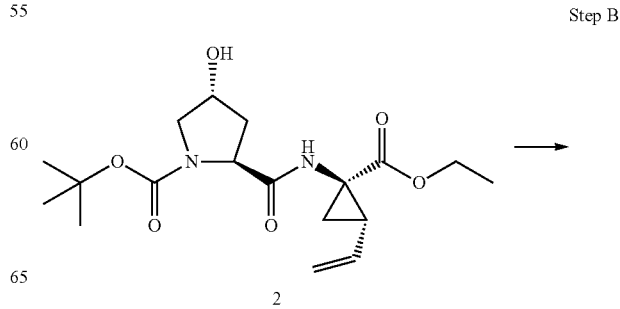

Step B

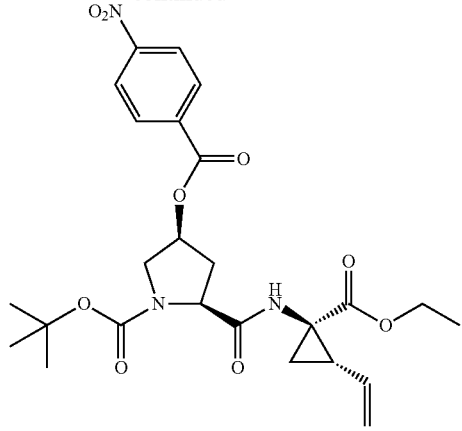

3

Compound 2 (6.13 g, 16.6 mmol), 4-nitrobenzoic acid (4.17 g, 25 mmol) and PPh$_3$ (6.55 g, 25 mmol) was dissolved in THF (130 mL). The solution was cooled to 0° C. and DIAD (5.1 g, 25 mmol) was added slowly. The cooling was then removed and the mixture was left at ambient condition for 12 h. Aqueous sodium hydrogen carbonate (60 mL) was added and the mixture was extracted with dichloromethane, dried (Na$_2$SO$_4$) and evaporated. Purification by flash chromatography (gradient pentane/ether, 2:1 to pentane/ether/methanol, 30:68:2) provided 6.2 g (72%) of the desired product 3: m/z=518 (M+H)$^+$.

Step C

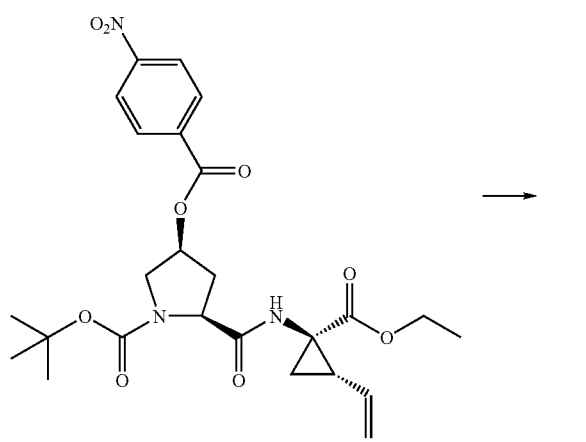

4

Compound 3 (6.2 g, 12 mmol) was dissolved in an ice-cold mixture of trifluoroacetic acid 33% in dichloromethane. The ice-bath was then removed and the mixture was left at room temperature for 1.5 h. The solvent was evaporated, and then the residue was partitioned between 0.25 M sodium carbonate and dichloromethane, dried (Na$_2$SO$_4$) and evaporated to give 4.8 g (95%) of the target product 4 as a yellowish powder: m/z=418 (M+H)$^+$.

Step D

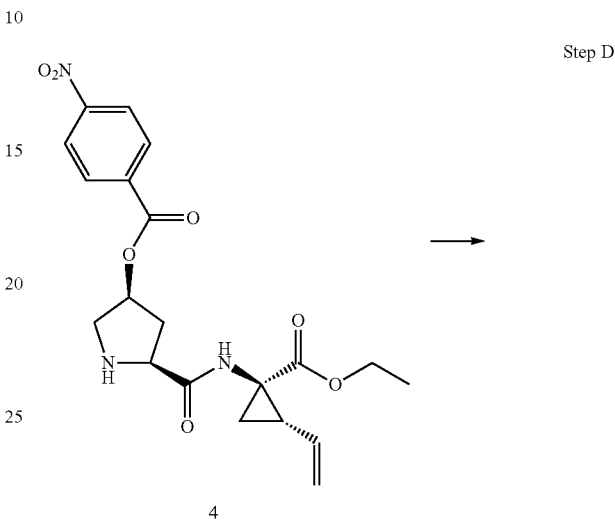

4

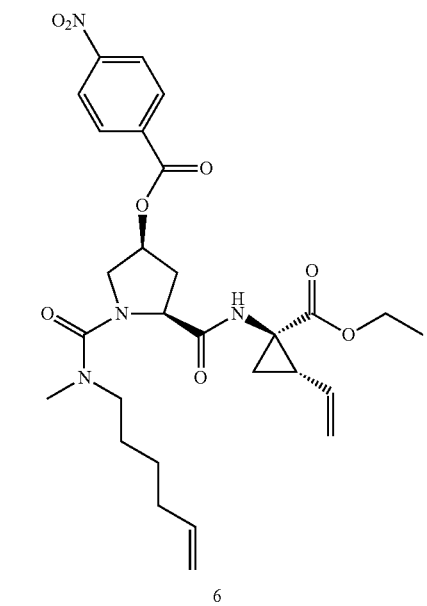

6

A tablespoon of sodium hydrogen carbonate was added to a solution of 4 (4.5 g, 10.8 mmol) in THF (160 mL). Then, phosgene (11.3 mL, 20% in toluene) was added. The mixture was stirred vigorously for 1 h, then filtered and re-dissolved in dichloromethane (160 mL). Sodium hydrogen carbonate (a tablespoon) was added followed by the N-methyl-N-hexen-5-yl hydrochloride (2.9 g, 21.6 mmol). The resulting reaction mixture was stirred at room temperature overnight. Workup and purification by flash chromatography (gradient ether to ether/methanol 97:3) gave 5.48 g (91%) of the target product 6: m/z=557 (M+H)$^+$.

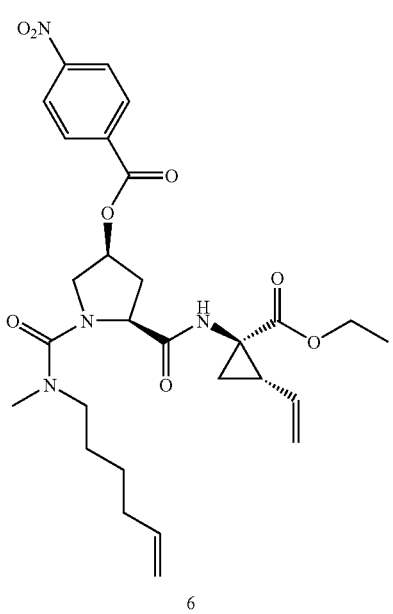

6

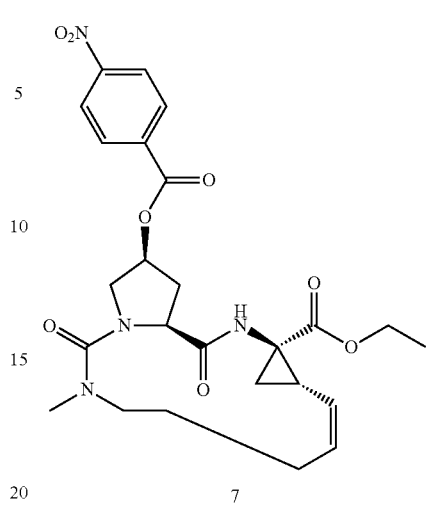

7

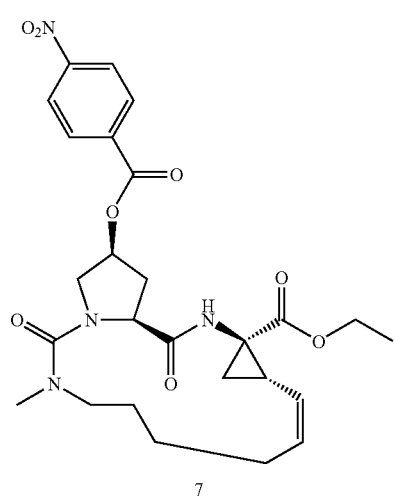

7

Compound 6 (850 mg, 1.53 mmol) was dissolved in 1.5 L of degassed and dried 1,2-dichloroethane and refluxed under argon atmosphere for 12 h. Scavenger (MP-TMT, P/N 800470 from Argonaut technologies, ½ teaspoon) was added and the mixture was stirred for 2 h, filtered and concentrated by reduced pressure. The crude product was crystallized from dichloromethane/n-hexane to yield 600 mg (74%) of the target product 7: m/z=529 (M+H)$^+$.

Step E

Step F

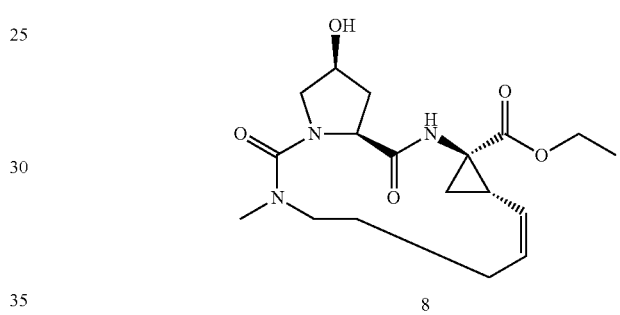

8

Compound 7 (200 mg, 0.38 mmol) was dissolved in a mixture of methanol/THF/water, 1:2:1, (20 mL) and cooled on ice-bath. Then, lithium hydroxide (1.9 mL, 1 M in water) was added slowly. The mixture was stirred for 4 h at 0° C., then neutralized with aqueous acetic acid (20 mL) and extracted with dichloromethane. The organic phase was washed with sodium bicarbonate, water, brine and dried (MgSO$_4$). Purification by column chromatography (methanol/dichloromethane, 96:4) gave 120 mg of the target compound 8 as a grayish powder: m/z=380 (M+H)$^+$.

Step G

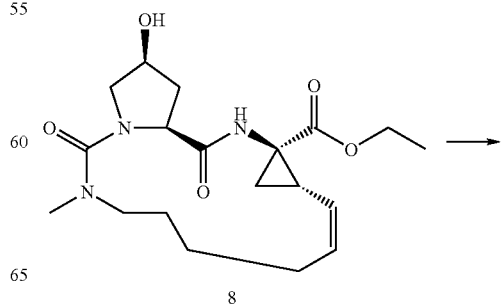

8

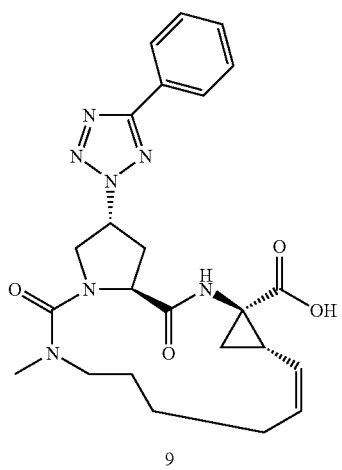

9

DIAD (218 µL, 1.11 mmol) is added at 0° C. under nitrogen atmosphere to a solution of 8 (280 mg, 0.738 mmol), 5-phenyl-1H-tetrazole (150 mg, 1.03 mmol) and triphenyl-phosphine (271 mg, 1.03 mmol) in dry THF (15 mL). Then, the reaction is warmed up to room temperature. After 1.5 h, the solvent is evaporated and the crude product is purified by flash column chromatography (AcOEt/Heptane, 3:7). This product is re-dissolved in THF (15 mL) and MeOH (10 mL). Then, a solution of LiOH (200 mg) in water (3 mL) is added. After 48 h, solvent is evaporated and the residue partitioned between water and ether. Aqueous layer is acidified (pH=3) and extracted with AcOEt, dried (MgSO$_4$) and evaporated. The residue is crystallized from ether to give the target compound 9.

Example 2

Preparation of N-[17-(5-phenyltetrazol-2-yl)-13-methyl-2,14-dioxo-3,13,15-triazatricyclo[13.3.0.0$^{4,6}$]octadec-7-ene-4-carbonyl](cyclopropyl)sulfonamide (10)

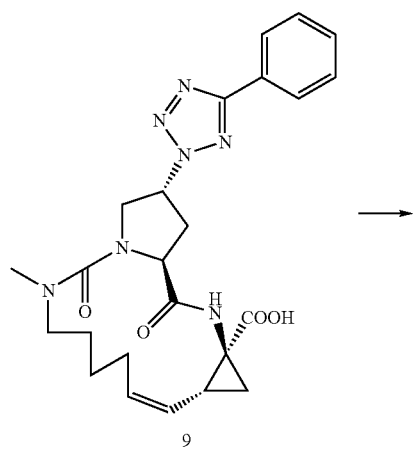

9

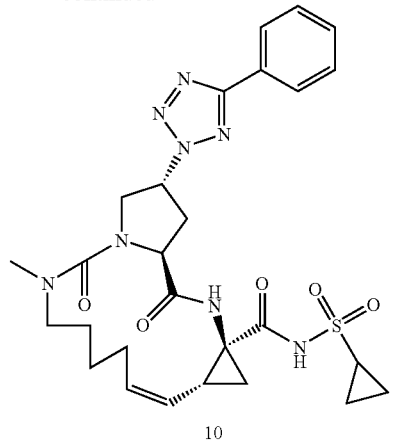

10

A mixture of 9 (50 mg, 0.104 mmol) and CDI (68 mg, 0.418 mmol) in dry THF (5 mL) is heated at reflux for 2 h under nitrogen. The reaction mixture is cooled to room temperature and cyclopropylsulfonamide (101 mg, 0.836 mmol) is added. Then, DBU (73 mg, 0.481 mmol) is added and the reaction mixture is stirred at room temperature for 1 h, and then heated at 55° C. for 24 h. Solvent is evaporated, and the residue partitioned between AcOEt and acidic water (pH=3). The crude material is purified by column chromatography (AcOEt/CH$_2$Cl$_2$/Petroleum ether, 1:1:1). The residue is crystallized in Et$_2$O, filtered to give the target compound contaminated with the cyclopropylsulfonamide. This material is triturated in 1.5 mL of water, filtered, washed with water and dried overnight in the high vacuum pump to give the target compound.

Example 3

Preparation of 17-(5-phenyltetrazol-2-yl)-13-methyl-2,14-dioxo-3,13-diazatricyclo[13.3.0.0$^{4,6}$]octadec-7-ene-4-carboxylic acid (9)

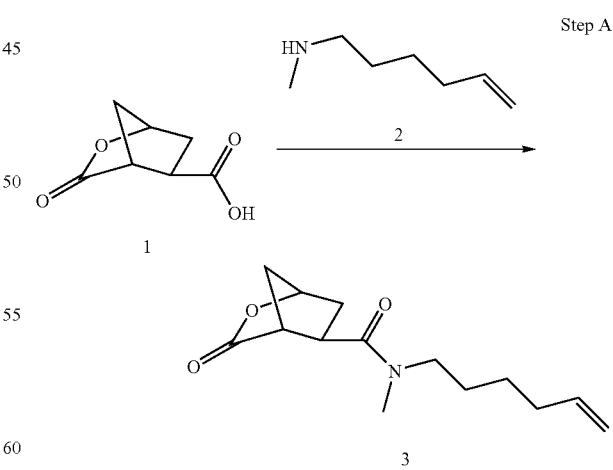

Step A

3-Oxo-2-oxa-bicyclo[2.2.1]heptane-5-carboxylic acid (1, 500 mg, 3.2 mmol) in 4 mL DMF was added at 0° C. to HATU (1.34 g, 3.52 mmol) and N-methylhex-5-enylamine (435 mg, 3.84 mmol) in DMF (3 mL), followed by DIEA. After stirring for 40 min at 0° C., the mixture was stirred at room temperature for 5 h. Then, the solvent was evaporated, the residue dissolved in EtOAc (70 mL) and washed with saturated NaHCO₃ (10 mL). The aqueous phase was extracted with EtOAc (2×25 mL). The organic phases were combined, washed with saturated NaCl (20 mL), dried (Na₂SO₄), and evaporated. Purification by flash chromatography (EtOAc/petroleum ether, 2:1) afforded 550 mg (68%) of the target product as a colorless oil: m/z=252 (M+H)⁺.

The 1-(amino)-2-(vinyl)cyclopropanecarboxylic acid ethyl ester hydrochloride (4.92 g, 31.7 mmol) and HATU (12.6 g, 33.2 mmol) were added to 4 (8.14 g, 30.2 mmol). The mixture was cooled in an ice bath under argon, and then DMF (100 mL) and DIPEA (12.5 mL, 11.5 mmol) were successively added. After 30 min at 0° C., the solution was stirred at room temperature for an additional 3 h. Then, the reaction mixture was partitioned between EtOAc and water, washed successively with 0.5 N HCl (20 mL) and saturated NaCl (2×20 mL), and dried (Na₂SO₄). Purification by flash chromatography (AcOEt/CH₂Cl₂/Petroleum ether, 1:1:1) afforded 7.41 g (60%) of the target product 6 as a colorless oil: m/z=407 (M+H)⁺.

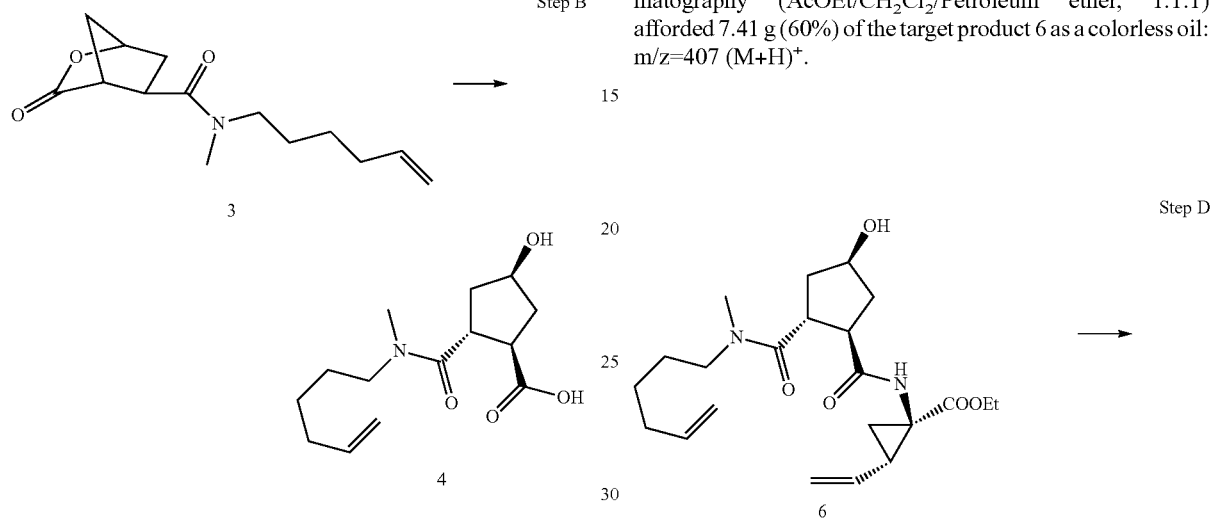

A solution of LiOH (105 mg in 4 mL of water) was added at 0° C. to the lactone amide 3. After 1 h, the conversion was completed (HPLC). The mixture was acidified to pH 2-3 with 1N HCl, extracted with AcOEt, dried (MgSO₄), evaporated, co-evaporated with toluene several times, and dried under high vacuum overnight to give 520 mg (88%) of the target product: m/z=270 (M+H)⁺.

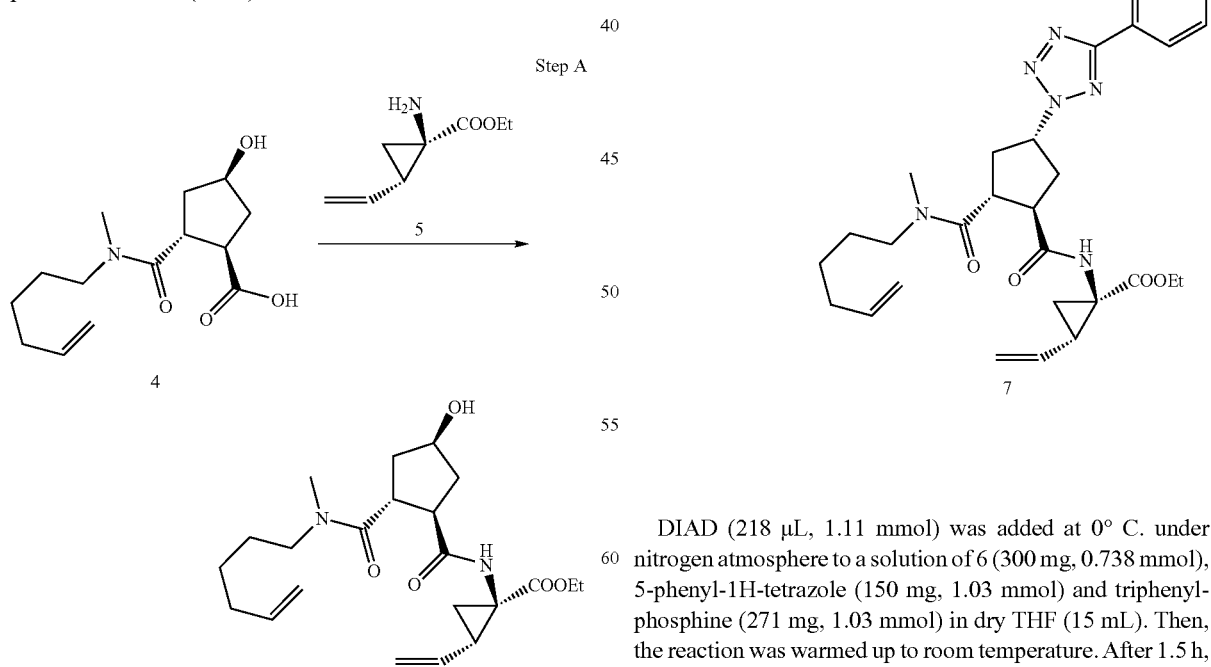

DIAD (218 µL, 1.11 mmol) was added at 0° C. under nitrogen atmosphere to a solution of 6 (300 mg, 0.738 mmol), 5-phenyl-1H-tetrazole (150 mg, 1.03 mmol) and triphenylphosphine (271 mg, 1.03 mmol) in dry THF (15 mL). Then, the reaction was warmed up to room temperature. After 1.5 h, the solvent was evaporated and the crude product was purified by flash column chromatography (AcOEt/Heptane, 3:7) to give 142 mg (43%) of the target product 7: m/z=535 (M+H)⁺.

Step E

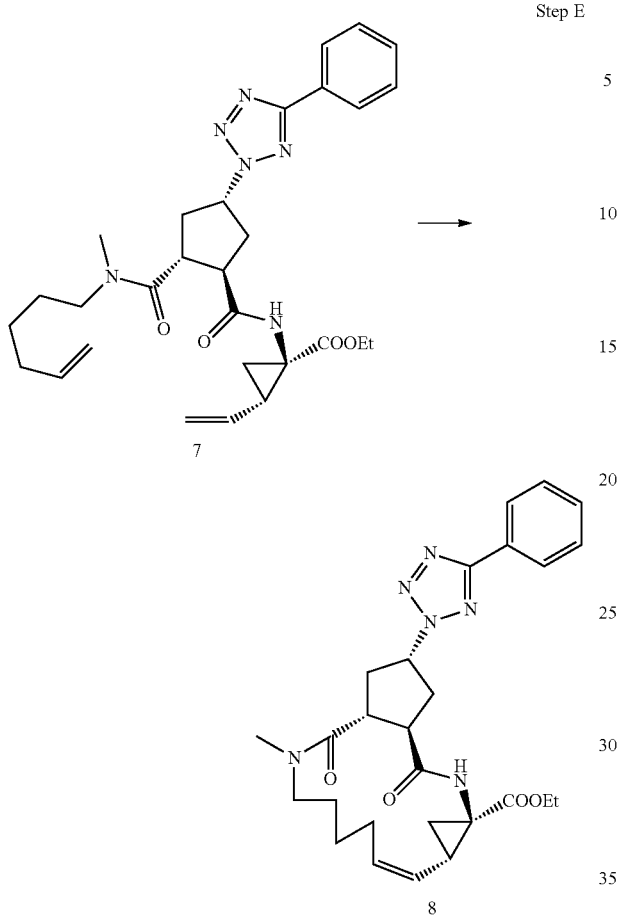

A solution of 7 (175 mg, 0.33 mmol) and Hoveyda-Grubbs 1st generation catalyst (39 mg, 0.066 mmol) in dried and degassed 1,2-dichloroethane (200 mL) was heated at 70° C. under nitrogen for 12 h. Then, the solvent was evaporated and the residue purified by silica gel chromatography (Petroleum ether/CH$_2$Cl$_2$/Et$_2$O; 3:1:1) to give 83 mg (50%) of the target product: m/z=507 (M+H)$^+$.

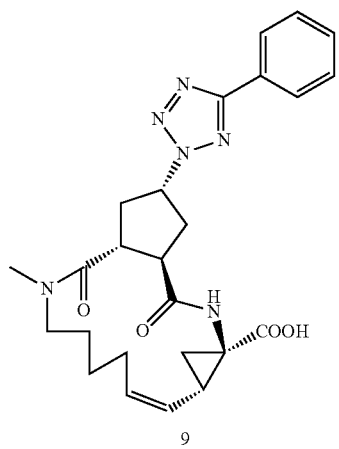

A solution of LiOH (200 mg) in water (3 mL) was added to a stirred solution of 8 in THF (15 mL) and MeOH (10 mL). After 48 h, solvent was evaporated and the residue partitioned between water and ether. Aqueous layer was acidified (pH=3) and extracted with AcOEt, dried (MgSO$_4$) and evaporated. The residue was crystallized from ether to give 68 mg (87%) of the target compound 9: m/z=479 (M+H)$^+$.

Example 4

Preparation of N-[17-(5-phenyltetrazol-2-yl)-13-methyl-2,14-dioxo-3,13-diazatricyclo[13.3.0.0$^{4,6}$]octadec-7-ene-4-carbonyl](cyclopropyl)sulfonamide (10)

Step F

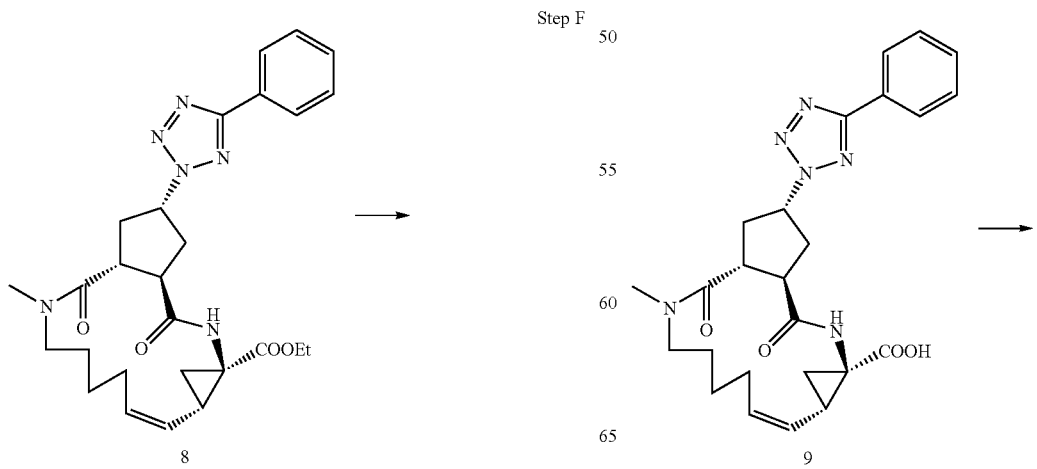

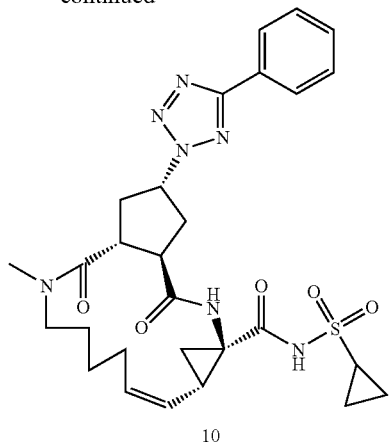

10

A mixture of 9 (50 mg, 0.104 mmol) and CDI (68 mg, 0.418 mmol) in dry THF (5 mL) was heated at reflux for 2 h under nitrogen. The reaction mixture was cooled to room temperature and cyclopropylsulfonamide (101 mg, 0.836 mmol) was added. Then, DBU (73 mg, 0.481 mmol) was added and the reaction mixture was stirred at room temperature for 1 h, and then heated at 55° C. for 24 h. Solvent was evaporated, and the residue partitioned between AcOEt and acidic water (pH=3). The crude material was purified by column chromatography (AcOEt/$CH_2Cl_2$/Petroleum ether, 1:1:1). The residue was crystallized in $Et_2O$, filtered to give the target compound contaminated with the cyclopropylsulfonamide. This material was triturated in 1.5 mL of water, filtered, washed with water and dried overnight in the high vacuum pump to give 28 mg (46%) of the target compound as a white powder: m/z=582 $(M+H)^+$.

Example 5

Synthesis of 3-Oxo-2-oxa-bicyclo[2.2.1]heptane-5-carboxylic acid tert-butyl ester (12)

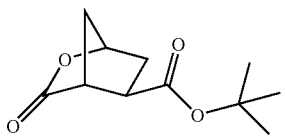

DMAP (14 mg, 0.115 mmol) and $Boc_2O$ (252 mg, 1.44 mmol) was added to a stirred solution of 11 (180 mg, 1.15 mmol) in 2 mL $CH_2Cl_2$ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) which gave the title compound (124 mg, 51%) as white crystals.

$^1$H-NMR (300 MHz, $CD_3OD$) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, $CD_3OD$) δ 27.1, 33.0, 37.7, 40.8, 46.1, 81.1, 81.6, 172.0, 177.7.

Alternative method for the preparation of compound 12

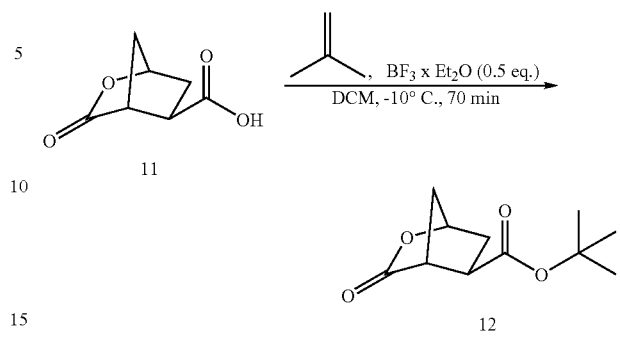

Compound 11 (13.9 g, 89 mmol) was dissolved in dichloromethane (200 ml) and then cooled to approximately −10° C. under nitrogen. Isobutylene was then bubbled into the solution until the total volume had increased to approximately 250 ml which gave a "clowdy solution". $BF_3×Et_2O$ (5.6 ml, 44.5 mmol, 0.5 eq.) was added and the reaction mixture was kept at approximately −10° C. under nitrogen. After 10 min, a clear solution was obtained. The reaction was monitored by TLC (EtOAc-Toluene 3:2 acidified with a few drops of acetic acid and hexane-EtOAc 4:1, staining with basic permanganate solution). At 70 min only traces of compound 11 remained and aq. saturated $NaHCO_3$ (200 ml) was added to the reaction mixture, which was then stirred vigorously for 10 min. The organic layer was washed with saturated $NaHCO_3$ (3×200 ml) and brine (1×150 ml), then dried with sodium sulfite, filtered and concentrated into an oil containing small droplets. Upon addition of hexane to the residue the product crashed out. Addition of more hexane and heating to reflux gave a clear solution from which the product crystallized. The crystals were collected by filtration and was washed with hexane (rt), then air-dried for 72 h giving colourless needles (12.45 g, 58.7 mmol, 66% from first harvest).

Example 6

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion ($neo^R$, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 μM NS4A cofactor and inhibitor at 30° C. for 10 min, whereupon the reaction was initiated by addition of 0.5 μM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures. [Liu, 1999 Analytical Biochemistry 267 331-335]. Ki values were estimated by non-linear regression analysis (GraFit, Erithacus Software, Staines, MX, UK), using a model for competitive inhibition and a fixed value for Km (0.15 μM). A minimum of two replicates was performed for all measurements.

The following Table 1 lists compounds that were prepared according to any one of the above examples. The activities of the compounds tested are also depicted in Table 1.

| Compound nr. | Example nr. | EC$_{50}$ (μM) Replicon assay | Ki (nM) Enzymatic assay |
| --- | --- | --- | --- |
| 9 | Example 3 | >10 | >1000 |
| 10 | Example 4 | 3.427 | 30 |

The invention claimed is:

1. A compound having the formula

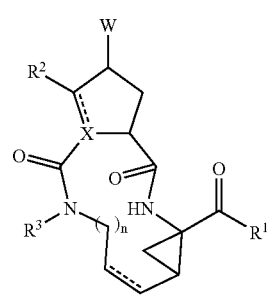

(I)

an N-oxide, salt, or stereoisomer thereof,
wherein the salt of formula (I) does not include a solvate;
wherein each dashed line (represented by - - - - -) represents an optional double bond;
X is N;
$R^1$ is —$OR^{11}$, or —NH—$SO_2R^{12}$;
$R^2$ is hydrogen;
$R^3$ is hydrogen, $C_{1-6}$alkyl, $C_{1-6}$alkoxy$C_{1-6}$alkyl, or $C_{3-7}$cycloalkyl;
n is 3, 4, 5, or 6;
W is a heterocycle of formula

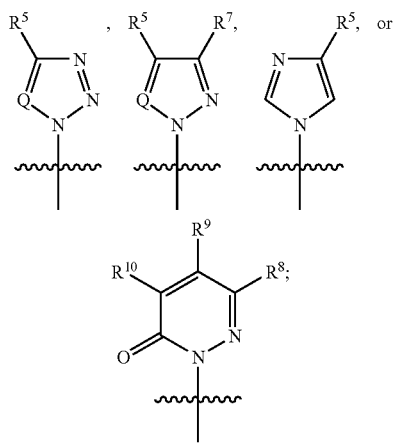

Q is N or $CR^4$;
$R^4$ is hydrogen; phenyl optionally substituted with $C_{1-6}$alkyl or with $C_{1-6}$alkoxy; thiazolyl optionally substituted with $C_{1-6}$alkyl; or pyridyl;
$R^5$ is phenyl optionally substituted with $C_{1-6}$alkyl or with $C_{1-6}$alkoxy; thiazolyl optionally substituted with $C_{1-6}$alkyl; or pyridyl;
one of $R^6$, $R^7$ is phenyl optionally substituted with $C_{1-6}$alkyl or with $C_{1-6}$alkoxy; thiazolyl optionally substituted with $C_{1-6}$alkyl; or pyridyl; while the other of $R^6$, $R^7$ is hydrogen; phenyl optionally substituted with $C_{1-6}$alkyl or with $C_{1-6}$alkoxy; thiazolyl optionally substituted with $C_{1-6}$alkyl; or pyridyl;
one of $R^8$, $R^9$, $R^{10}$ is phenyl optionally substituted with $C_{1-6}$alkyl or with $C_{1-6}$alkoxy; thiazolyl optionally substituted with $C_{1-6}$alkyl; or pyridyl; while the other two of $R^8$, $R^9$, $R^{10}$ independently are hydrogen; phenyl optionally substituted with $C_{1-6}$alkyl or with $C_{1-6}$alkoxy; thiazolyl optionally substituted with $C_{1-6}$alkyl; or pyridyl;

$R^{11}$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;

$R^{12}$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;

each aryl as a group or part of a group is phenyl, optionally substituted with one, two or three substituents selected from halo, hydroxy, nitro, cyano, carboxyl, $C_{1-6}$alkyl, $C_{1-6}$alkoxy, $C_{1-6}$alkoxyC$_{1-6}$alkyl, $C_{1-6}$alkylcarbonyl, amino, mono- or diC$_{1-6}$alkylamino, azido, mercapto, polyhaloC$_{1-6}$alkyl, polyhaloC$_{1-6}$alkoxy, $C_{3-7}$cycloalkyl, pyrrolidinyl, piperidinyl, piperazinyl, 4-C$_{1-6}$alkyl-piperazinyl, 4-C$_{1-6}$alkylcarbonyl-piperazinyl, morpholinyl; wherein the morpholinyl and piperidinyl groups may be optionally substituted with one or with two $C_{1-6}$alkyl radicals; and each Het as a group or part of a group is a 5 or 6 membered saturated, partially unsaturated or completely unsaturated heterocyclic ring containing 1 to 4 heteroatoms each independently selected from nitrogen, oxygen and sulfur, and being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxyC$_{1-6}$alkyl, $C_{1-6}$alkylcarbonyl, amino, mono- or diC$_{1-6}$alkylamino, azido, mercapto, polyhaloC$_{1-6}$alkyl, polyhaloC$_{1-6}$alkoxy, $C_{3-7}$cycloalkyl, pyrrolidinyl, piperidinyl, piperazinyl, 4-C$_{1-6}$alkyl-piperazinyl, 4-C$_{1-6}$alkylcarbonyl-piperazinyl, morpholinyl; wherein the morpholinyl and piperidinyl groups may be optionally substituted with one or with two $C_{1-6}$alkyl radicals.

2. A compound according to claim 1, wherein the compound has the formula (I-c):

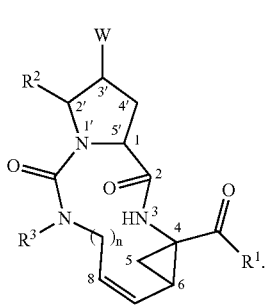

(I-c)

3. A compound according to claim 1, wherein W is

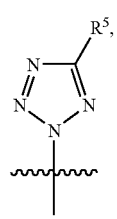

and $R^5$ is phenyl, 3-methoxyphenyl, 3,4-dimethoxyphenyl, 4-ethoxyphenyl, 4-propoxyphenyl, 4-butoxyphenyl, 2-pyridyl, 3-pyridyl, or 4-pyridyl.

4. A compound according to claim 1, wherein W is

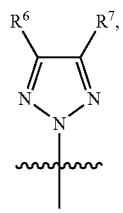

wherein $R^6$ is phenyl, m-methoxyphenyl, 2-pyridyl, 3-pyridyl, or 2-thiazolyl; and
$R^7$ is phenyl, p-methoxyphenyl, or 4-ethoxyphenyl.

5. A compound according to claim 1, wherein
(a) $R^1$ is —$OR^{11}$, wherein $R^{11}$ is $C_{1-6}$alkyl or hydrogen; or
(b) $R^1$ is —NHS(=O)$_2$R$^{12}$, wherein $R^{12}$ is methyl, cyclopropyl, or phenyl.

6. A compound according to claim 1, other than an N-oxide, or salt.

7. A combination comprising
(a) a compound as defined in claim 1 or a pharmaceutically acceptable salt thereof; and
(b) ritonavir, or a pharmaceutically acceptable salt thereof.

8. A pharmaceutical composition comprising a carrier, and as active ingredient an anti-virally effective amount of a compound as claimed in claim 1.

9. A method of inhibiting HCV replication in a warm-blooded animal said method comprising the administration of an effective amount of a compound according to claim 1.

10. A process for preparing a compound as claimed in claim 1, wherein said process comprises:
(a) preparing a compound of formula (I) wherein the bond between $C_7$ and $C_8$ is a double bond, which is a compound of formula (I-i), by forming a double bond between $C_7$ and $C_8$, in particular via an olefin metathesis reaction, with concomitant cyclization to the macrocycle as outlined in the following reaction scheme:

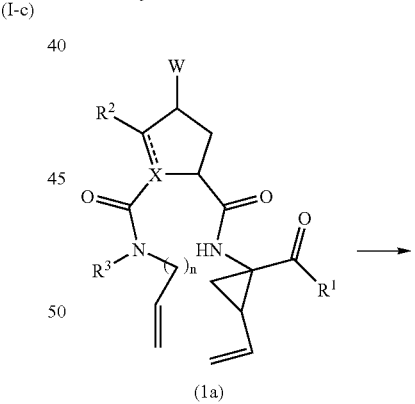

(1a)

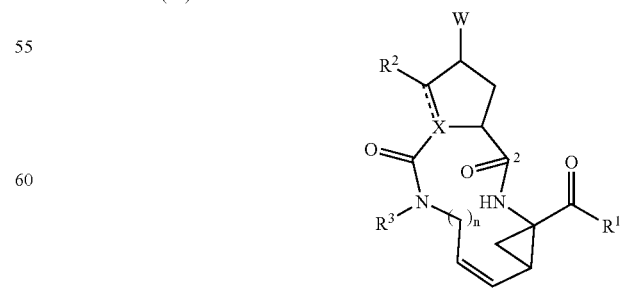

(I-i)

(b) converting a compound of formula (I-i) to a compound of formula (I) wherein the link between C7 and C8 in the macrocycle is a single bond, i.e. a compound of formula (I-j):

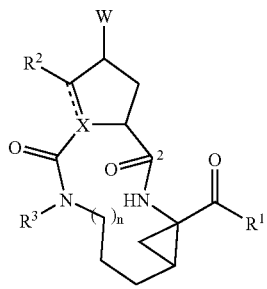

(I-j)

by a reduction of the C7-C8 double bond in the compounds of formula (I-i);

(c) preparing a compound of formula (I) wherein $R^1$ represents —$NHSO_2R^{12}$, said compounds being represented by formula (I-k-1), by forming an amide bond between a intermediate (2a) and an sulfonylamine (2b), or preparing a compound of formula (I) wherein $R^1$ represents —$OR^{11}$, i.e. a compound (I-k-2), by forming an ester bond between an intermediate (2a) and an alcohol (2c) as outlined in the following scheme wherein G represents a group:

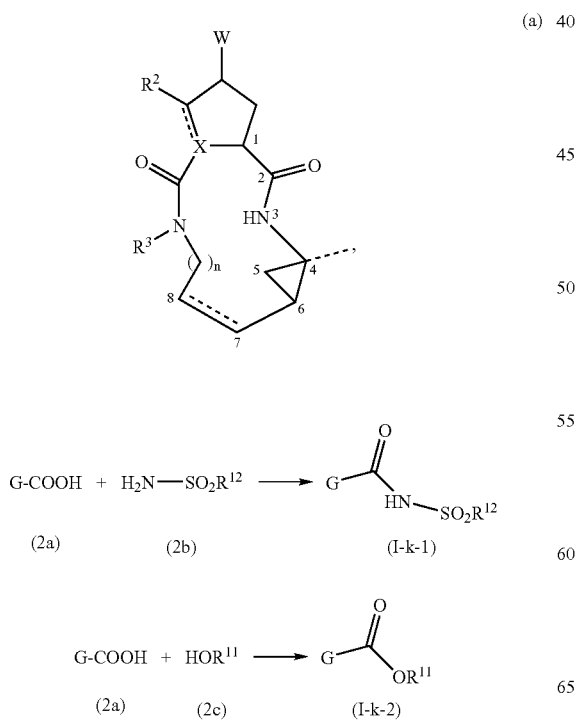

(d) reacting an intermediate (4a) with an intermediate (4b) as outlined in the following reaction scheme:

(4a)  W—H (4b)

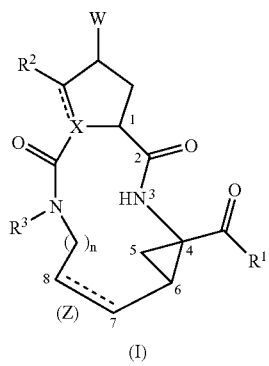

(I)

wherein Y in (4a) represents hydroxy or a leaving group; which reaction in particular is an O-arylation reaction wherein Y represents a leaving group, or a Mitsunobu reaction, wherein Y represents hydroxy;

(e) preparing a compound of formula (I) wherein $R^3$ is hydrogen, said compound being represented by (I-l), from a corresponding nitrogen-protected intermediate (3a), wherein PG represents a nitrogen protecting group:

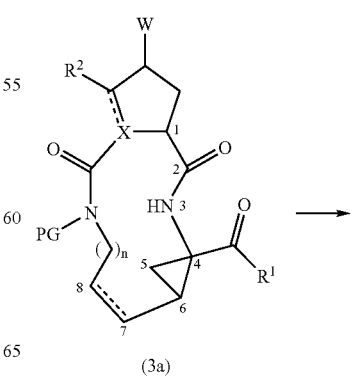

(3a)

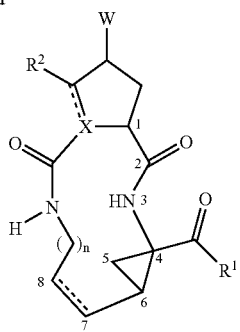

(I-1)

(f) converting compounds of formula (I) into each other by a functional group transformation reaction; or (g) preparing a salt form by reacting the free form of a compound of formula (I) with an acid or a base.

11. A pharmaceutical composition comprising a carrier, and as active ingredient an anti-virally effective amount of a combination according to claim 7.

12. A method of inhibiting HCV replication in a warm-blooded animal said method comprising the administration of an effective amount of the combination according to claim 7.

* * * * *